(12) United States Patent
Bader

(10) Patent No.: US 10,456,346 B2
(45) Date of Patent: Oct. 29, 2019

(54) COSMETIC FORMULATIONS FOR TOPICAL APPLICATIONS CONTAINING ERYTHROPOIETIN-DERIVED MOLECULES

(71) Applicant: ASC REGENITY LTD., London (GB)

(72) Inventor: Augustinus Bader, Parthenstein (DE)

(73) Assignee: ASC REGENITY LTD., London (GB)

( * ) Notice: Subject to any disclaimer, the term of this patent is extended or adjusted under 35 U.S.C. 154(b) by 0 days.

(21) Appl. No.: 16/346,553

(22) PCT Filed: Nov. 7, 2017

(86) PCT No.: PCT/EP2017/001289
§ 371 (c)(1),
(2) Date: May 1, 2019

(87) PCT Pub. No.: WO2018/086732
PCT Pub. Date: May 17, 2018

(65) Prior Publication Data
US 2019/0254948 A1    Aug. 22, 2019

(30) Foreign Application Priority Data
Nov. 10, 2016  (EP) ................................. 16002375

(51) Int. Cl.
*A61K 38/00* (2006.01)
*A61K 8/64* (2006.01)
*A61Q 19/08* (2006.01)

(52) U.S. Cl.
CPC ............... *A61K 8/64* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 7,910,547 B2 | 3/2011 | Bader | |
| 9,101,586 B2 | 8/2015 | Bader | |
| 2009/0221482 A1* | 9/2009 | Cerami | C07K 14/71 514/7.7 |
| 2013/0236432 A1 | 9/2013 | Bader | |

FOREIGN PATENT DOCUMENTS

| | | |
|---|---|---|
| CN | 102 205 114 A | 10/2011 |
| EP | 2 371 855 A1 | 10/2011 |
| EP | 2 933 264 A2 | 10/2015 |
| WO | 2004/001023 A2 | 12/2003 |
| WO | 2005/063965 A1 | 7/2005 |
| WO | 2007/019545 A2 | 2/2007 |
| WO | 2009/022338 A2 | 2/2009 |
| WO | 2009/083203 A2 | 7/2009 |
| WO | 2012/003960 A1 | 1/2012 |
| WO | 2015/174601 A1 | 11/2015 |

OTHER PUBLICATIONS

Michael Brines et al., "Emerging Biological Roles for Erythropoietin in the Nervous System", Nature Publishing Group, vol. 6, Jun. 2005, pp. 484-494.
Lei Wang et al., "Treatment of Stroke with Erythropoietin Enhances Neurogenisis and Angiogenesis and Improves Neurological Function in Rats", Stroke, vol. 35, Apr. 22, 2004, pp. 1732-1737, See Spec., p. 2.
Michael Brines et al., "Erythropoietin Mediates Tissue Protection Through an Erythropoietin and Common β-subunit Heteroreceptor", PNAS, vol. 101, No. 41, Oct. 12, 2004, pp. 14907-14912, See Spec., p. 2.
Priya Giri et al., "Skin Regeneration in Deep Second-Degree Scald Injuries Either by Infusion Pumping or Topical Application of Recombinant Human Erythropoietin Gel", Drug Design, Development and Therapy, vol. 9, 2015, pp. 2565-2579, See Spec., p. 2.
Christina Gunter et al., "First Results on Three Patients Treated with Topical Recombinant Human Erythropoietin (rhEPO) to Improve Would Healing in Diabetic Foot Ulcers", Journal of Transplantation & Stem Cell Biology, vol. 2, Issue: 1, Jan. 2015, pp. 1-4, See Spec., p. 2.
Saher Hamed et al., "Erythropoietin, A Novel Repurposed Drug: An Innovative Treatment for Wound Healing in Pateitns with Diabetes Mellitus", Wound Repair and Regeneration, vol. 22, 2014, pp. 23-33, See Spec., p. 2.
https://www.canfieldsci.com/imaging-systems/visia-complexion-analysis/, Visia Complexion Analysis Brochure, Accessed Apr. 2019, See Spec., p. 25.
Michael Brines et al., "Nonerythropoietic, Tissue-Protective Peptides Derived from the Tertiary Structure of Erythropoietin", PNAS, National Academy of Sciences, US, vol. 105, No. 31, Aug. 5, 2008, pp. 10925-10930, See International Search.
Francis Dumont et al., "Non-Eruthropoietic Tissue-Protective Peptides Derived from Erythropoietin: WO2009094172", Expert Opinion on Therapeutic Patents, vol. 20, No. 5, Mar. 2, 2010, pp. 715-723, See International Search.
Zübeyde- Erbayraktaret al., "Nonerythropoietic Tissue Protective Compounds Are Highly Effective Facilitators of Wound Healing", Molecular Medicine, vol. 15, No. 7-8, Jan. 1, 2009, p. 1, See International Search.

(Continued)

*Primary Examiner* — Jeanette M Lieb
(74) *Attorney, Agent, or Firm* — Davis & Bujold PLLC; Michael J. Bujold

(57) ABSTRACT

The invention relates to cosmetic formulations and new peptide related entities designed for the cosmetic treatment of the human skin. In more detail, the invention is related to peptides that target CD90 positive tissue cells and correspond to or derive from the partial sequence of erythropoietin (EPO) but do not substantially elicit a hematopoietic but a tissue regenerative and protective effect. In particular, the invention discloses EPO-derived tissue-protective peptides in functional relation to lipid structures and agents that trigger vasculature relaxation and promote transdermal transport of the polypeptide entities to the targeted skin cells.

14 Claims, 3 Drawing Sheets
Specification includes a Sequence Listing.

(56) References Cited

OTHER PUBLICATIONS

International Search Report Corresponding to PCT/EP2017/001289 dated Feb. 5, 2018.
Written Opinion Corresponding to PCT/EP2017/001289 dated Feb. 5, 2018.

* cited by examiner

SEQUENCE LISTING

<160> NUMBER OF SEQ ID NOS: 84

<210> SEQ ID NO 1
<211> LENGTH: 166
<212> TYPE: PRT
<213> ORGANISM: Homo sapiens

```
<220> FEATURE:
<223> OTHER INFORMATION: human erythropoietin (hEPO)

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 25
<212> TYPE: PRT
<213> ORGANISM: Artificial Sequence
<220> FEATURE:
<223> OTHER INFORMATION: Fragment of human erythropoietin

<400> SEQUENCE: 2

Gln Gln Ala Val Glu Val Trp Gln Gly Leu Ala Leu Leu Ser Glu Ala
1               5                   10                  15

Val Leu Arg Gly Gln Ala Leu Leu Val
            20                  25

<210> SEQ ID NO 3
<211> LENGTH: 16
<212> TYPE: PRT
<213> ORGANISM: Artificial Sequence
<220> FEATURE:
<223> OTHER INFORMATION: Fragment of human erythropoietin

<400> SEQUENCE: 3

Arg Tyr Leu Leu Glu Ala Lys Glu Ala Glu Asn Ile Thr Thr Gly Cys
1               5                   10                  15

<210> SEQ ID NO 4
<211> LENGTH: 23
<212> TYPE: PRT
<213> ORGANISM: Artificial Sequence
<220> FEATURE:
<223> OTHER INFORMATION: Fragment of human erythropoietin

<400> SEQUENCE: 4

Ala Pro Pro Arg Leu Ile Cys Asp Ser Arg Val Leu Glu Arg Tyr Leu
1               5                   10                  15
```

Leu Glu Ala Lys Glu Ala Glu
            20

<210> SEQ ID NO 5
<211> LENGTH: 29
<212> TYPE: PRT
<213> ORGANISM: Artificial Sequence
<220> FEATURE:
<223> OTHER INFORMATION: synthetic, derived from interface of EPO and
      EPO receptor, or the helix structure, or share consensus sequence
      with fragments of type I cytokine receptor, all having no
      significant heamtopoietic property

<400> SEQUENCE: 5

Phe Arg Lys Leu Phe Arg Val Tyr Ser Asn Phe Leu Arg Gly Lys Leu
1               5                   10                  15

Lys Leu Tyr Thr Gly Glu Ala Cys Arg Thr Gly Asp Arg
            20                  25

<210> SEQ ID NO 6
<211> LENGTH: 23
<212> TYPE: PRT
<213> ORGANISM: Artificial Sequence
<220> FEATURE:
<223> OTHER INFORMATION: synthetic, derived from interface of EPO and
      EPO receptor, or the helix structure, or share consensus sequence
      with fragments of type I cytokine receptor, all having no
      significant heamtopoietic property

<400> SEQUENCE: 6

Met Glu Val Gly Gln Gln Ala Val Glu Val Trp Gln Gly Leu Ala Leu
1               5                   10                  15

Leu Ser Glu Ala Val Leu Arg
            20

<210> SEQ ID NO 7
<211> LENGTH: 18
<212> TYPE: PRT
<213> ORGANISM: Artificial Sequence
<220> FEATURE:
<223> OTHER INFORMATION: synthetic, derived from interface of EPO and
      EPO receptor, or the helix structure, or share consensus sequence
      with fragments of type I cytokine receptor, all having no
      significant heamtopoietic property

<400> SEQUENCE: 7

Thr Tyr Ser Cys His Phe Gly Pro Leu Thr Trp Val Cys Lys Pro Gln
1               5                   10                  15

Gly Gly

<210> SEQ ID NO 8
<211> LENGTH: 15
<212> TYPE: PRT
<213> ORGANISM: Artificial Sequence
<220> FEATURE:
<223> OTHER INFORMATION: synthetic, derived from interface of EPO and
      EPO receptor, or the helix structure, or share consensus sequence
      with fragments of type I cytokine receptor, all having no
      significant heamtopoietic property

<400> SEQUENCE: 8

Lys Leu Lys Leu Tyr Thr Gly Glu Ala Cys Arg Thr Gly Asp Arg
1               5                   10                  15

<210> SEQ ID NO 9
<211> LENGTH: 14

```
<212> TYPE: PRT
<213> ORGANISM: Artificial Sequence
<220> FEATURE:
<223> OTHER INFORMATION: synthetic, derived from interface of EPO and
      EPO receptor, or the helix structure, or share consensus sequence
      with fragments of type I cytokine receptor, all having no
      significant heamtopoietic property

<400> SEQUENCE: 9

Trp Glu His Val Asn Ala Ile Gln Glu Ala Arg Arg Leu Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic, derived from interface of EPO and
      EPO receptor, or the helix structure, or share consensus sequence
      with fragments of type I cytokine receptor, all having no
      significant heamtopoietic property

<400> SEQUENCE: 10

His Ala Asp Arg Glu Leu Glu Lys Ile Gly Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: 'Peptide 0': EPO derived synthetic peptide
      having tissue protective property, known from EP 2371855

<400> SEQUENCE: 11

Gln Glu Gln Leu Glu Arg Ala Leu Asn Ser Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: 'Peptide 2': new synthetic peptide with
      tissue-protective property, variant of "Peptide 0

<400> SEQUENCE: 12

Asn Glu Gln Leu Glu Arg Ala Leu Asn Thr Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: 'Peptide 1': new synthetic peptide with
      tissue-protective property, variant of "Peptide 0

<400> SEQUENCE: 13

Asn Glu Gln Leu Glu Arg Ala Leu Asn Ser Thr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: 'Peptide 4': new synthetic peptide with
      tissue-protective property, variant of "Peptide 0
```

<400> SEQUENCE: 14

Gln Asp Gln Leu Glu Arg Ala Leu Asn Thr Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: 'Peptide 3': new synthetic peptide with
      tissue-protective property, variant of "Peptide 0

<400> SEQUENCE: 15

Gln Asp Gln Leu Glu Arg Ala Leu Asn Ser Thr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: new synthetic 11-mer peptides with
      tissue-protective property, variants of "Peptide 0;
<220> FEATURE:
<221> NAME/KEY: VARIANT
<222> LOCATION: 1
<223> OTHER INFORMATION: Xaa = Q or N
<220> FEATURE:
<221> NAME/KEY: VARIANT
<222> LOCATION: 2
<223> OTHER INFORMATION: Xaa = E or D
<220> FEATURE:
<221> NAME/KEY: VARIANT
<222> LOCATION: 3
<223> OTHER INFORMATION: Xaa = Q or N
<220> FEATURE:
<221> NAME/KEY: VARIANT
<222> LOCATION: 9
<223> OTHER INFORMATION: Xaa = Q or N
<220> FEATURE:
<221> NAME/KEY: VARIANT
<222> LOCATION: 10
<223> OTHER INFORMATION: Xaa = S or T
<220> FEATURE:
<221> NAME/KEY: VARIANT
<222> LOCATION: 11
<223> OTHER INFORMATION: Xaa = S or T

<400> SEQUENCE: 16

Xaa Xaa Xaa Leu Glu Arg Ala Leu Xaa Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: new synthetic 11-mer peptides with
      tissue-protective property, variants of "Peptide 0;
<220> FEATURE:
<221> NAME/KEY: VARIANT
<222> LOCATION: 1
<223> OTHER INFORMATION: Xaa = Q or N
<220> FEATURE:
<221> NAME/KEY: VARIANT
<222> LOCATION: 2
<223> OTHER INFORMATION: Xaa = E or D
<220> FEATURE:
<221> NAME/KEY: VARIANT
<222> LOCATION: 10
<223> OTHER INFORMATION: Xaa = S or T
<220> FEATURE:

```
<221> NAME/KEY: VARIANT
<222> LOCATION: 11
<223> OTHER INFORMATION: Xaa = S or T

<400> SEQUENCE: 17

Xaa Xaa Gln Leu Glu Arg Ala Leu Asn Xaa Xaa
1               5                   10

<210> SEQ ID NO 18
<211> LENGTH: 7
<212> TYPE: PRT
<213> ORGANISM: Artificial Sequence
<220> FEATURE:
<223> OTHER INFORMATION: new synthetic 7-mer peptides with
      tissue-protective property, variants of "Peptide 0;
<220> FEATURE:
<221> NAME/KEY: VARIANT
<222> LOCATION: 1
<223> OTHER INFORMATION: Xaa = Q or N
<220> FEATURE:
<221> NAME/KEY: VARIANT
<222> LOCATION: 7
<223> OTHER INFORMATION: Xaa = Q or N

<400> SEQUENCE: 18

Xaa Leu Glu Arg Ala Leu Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: new synthetic 9-mer peptides with
      tissue-protective property, variants of "Peptide 0;
<220> FEATURE:
<221> NAME/KEY: VARIANT
<222> LOCATION: 1
<223> OTHER INFORMATION: Xaa = E or D
<220> FEATURE:
<221> NAME/KEY: VARIANT
<222> LOCATION: 2
<223> OTHER INFORMATION: Xaa = Q or N
<220> FEATURE:
<221> NAME/KEY: VARIANT
<222> LOCATION: 8
<223> OTHER INFORMATION: Xaa = Q or N
<220> FEATURE:
<221> NAME/KEY: VARIANT
<222> LOCATION: 9
<223> OTHER INFORMATION: Xaa = S or T

<400> SEQUENCE: 19

Xaa Xaa Leu Glu Arg Ala Leu Xaa Xaa
1               5

<210> SEQ ID NO 20
<211> LENGTH: 12
<212> TYPE: PRT
<213> ORGANISM: Artificial Sequence
<220> FEATURE:
<223> OTHER INFORMATION: 'Peptide 0' plus vasculature relaxation
      stimulating agent at 3' end;
<220> FEATURE:
<221> NAME/KEY: VARIANT
<222> LOCATION: 12
<223> OTHER INFORMATION: Xaa = R(arginine) or citrulline, or choline at
      3'-end

<400> SEQUENCE: 20

Gln Glu Gln Leu Glu Arg Ala Leu Asn Ser Ser Xaa
1               5                   10
```

```
<210> SEQ ID NO 21
<211> LENGTH: 13
<212> TYPE: PRT
<213> ORGANISM: Artificial Sequence
<220> FEATURE:
<223> OTHER INFORMATION: 'Peptide 0' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) if Xaa(13) = R, or Xaa =
      citrulline if Xaa(13) = citrullien, or Xaa = choline if Xaa(13) =
      vitamin B5 at 3'end
<220> FEATURE:
<221> NAME/KEY: VARIANT
<222> LOCATION: 13
<223> OTHER INFORMATION: Xaa = R(arginine) if Xaa(12) = R, or Xaa =
      citrulline if Xaa(12) = citrulline, or Xaa = vitamin B5 if
      Xaa(12) = choline at 3'-end

<400> SEQUENCE: 21

Gln Glu Gln Leu Glu Arg Ala Leu Asn Ser Ser Xaa Xaa
1               5                   10

<210> SEQ ID NO 22
<211> LENGTH: 14
<212> TYPE: PRT
<213> ORGANISM: Artificial Sequence
<220> FEATURE:
<223> OTHER INFORMATION: 'Peptide 0' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) at 3'-end
<220> FEATURE:
<221> NAME/KEY: VARIANT
<222> LOCATION: 13
<223> OTHER INFORMATION: Xaa = R(arginine); or Xaa = choline if
      Xaa(14) = Vitamin B5 at 3'-end
<220> FEATURE:
<221> NAME/KEY: VARIANT
<222> LOCATION: 14
<223> OTHER INFORMATION: Xaa = R(arginine) or citrulline or cholin or
      vitamin B5 at 3'-end

<400> SEQUENCE: 22

Gln Glu Gln Leu Glu Arg Ala Leu Asn Ser Ser Xaa Xaa Xaa
1               5                   10

<210> SEQ ID NO 23
<211> LENGTH: 15
<212> TYPE: PRT
<213> ORGANISM: Artificial Sequence
<220> FEATURE:
<223> OTHER INFORMATION: 'Peptide 0' plus vasculature relaxation
      stimulating agents at 3' end;
<220> FEATURE:
<221> NAME/KEY: VARIANT
<222> LOCATION: 12
<223> OTHER INFORMATION: Xaa = R (arginine) at 3'-end
<220> FEATURE:
<221> NAME/KEY: VARIANT
<222> LOCATION: 13
<223> OTHER INFORMATION: Xaa = R (arginine) at 3'-end
<220> FEATURE:
<221> NAME/KEY: VARIANT
<222> LOCATION: 14
<223> OTHER INFORMATION: Xaa = citrulline or choline-vitamin B5 at
      3'-end
<220> FEATURE:
<221> NAME/KEY: VARIANT
<222> LOCATION: 15
```

```
<223> OTHER INFORMATION: Xaa = citrulline at 3'-end if Xaa(14) is not
      choline

<400> SEQUENCE: 23

Gln Glu Gln Leu Glu Arg Ala Leu Asn Ser Ser Xaa Xaa Xaa Xaa
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: 'Peptide 0' plus vasculature relaxation
      stimulating agents (here: arginine) at 5'- and 3' end;

<400> SEQUENCE: 24

Arg Gln Glu Gln Leu Glu Arg Ala Leu Asn Ser Ser Arg
1               5                   10

<210> SEQ ID NO 25
<211> LENGTH: 15
<212> TYPE: PRT
<213> ORGANISM: Artificial Sequence
<220> FEATURE:
<223> OTHER INFORMATION: 'Peptide 0' plus vasculature relaxation
      stimulating agents at 5'- and 3' end;

<400> SEQUENCE: 25

Arg Arg Gln Glu Gln Leu Glu Arg Ala Leu Asn Ser Ser Arg Arg
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: 'Peptide 0' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline
<220> FEATURE:
<221> NAME/KEY: VARIANT
<222> LOCATION: 15
<223> OTHER INFORMATION: Xaa = citrulline

<400> SEQUENCE: 26

Xaa Arg Gln Glu Gln Leu Glu Arg Ala Leu Asn Ser Ser Arg Xaa
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: 'Peptide 0' plus vasculature relaxation
      stimulating agents at 5'- and 3' end;
<220> FEATURE:
<221> NAME/KEY: VARIANT
<222> LOCATION: 16
<223> OTHER INFORMATION: Xaa = choline or choline-vitamin B5

<400> SEQUENCE: 27

Arg Arg Gln Glu Gln Leu Glu Arg Ala Leu Asn Ser Ser Arg Arg Xaa
1               5                   10                  15

<210> SEQ ID NO 28
<211> LENGTH: 19
```

```
<212> TYPE: PRT
<213> ORGANISM: Artificial Sequence
<220> FEATURE:
<223> OTHER INFORMATION: 'Peptide 0' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5' end
<220> FEATURE:
<221> NAME/KEY: VARIANT
<222> LOCATION: 2
<223> OTHER INFORMATION: Xaa = citrulline at 5' end
<220> FEATURE:
<221> NAME/KEY: VARIANT
<222> LOCATION: 18
<223> OTHER INFORMATION: Xaa = citrulline at 3' end
<220> FEATURE:
<221> NAME/KEY: VARIANT
<222> LOCATION: 19
<223> OTHER INFORMATION: Xaa = citrulline at 3' end

<400> SEQUENCE: 28

Xaa Xaa Arg Arg Gln Glu Gln Leu Glu Arg Ala Leu Asn Ser Ser Arg
1               5                   10                  15

Arg Xaa Xaa

<210> SEQ ID NO 29
<211> LENGTH: 20
<212> TYPE: PRT
<213> ORGANISM: Artificial Sequence
<220> FEATURE:
<223> OTHER INFORMATION: 'Peptide 0' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5'-end
<220> FEATURE:
<221> NAME/KEY: VARIANT
<222> LOCATION: 2
<223> OTHER INFORMATION: Xaa = citrulline at 5'-end
<220> FEATURE:
<221> NAME/KEY: VARIANT
<222> LOCATION: 18
<223> OTHER INFORMATION: Xaa = citrulline at 3'-end
<220> FEATURE:
<221> NAME/KEY: VARIANT
<222> LOCATION: 19
<223> OTHER INFORMATION: Xaa = citrulline at 3'-end
<220> FEATURE:
<221> NAME/KEY: VARIANT
<222> LOCATION: 20
<223> OTHER INFORMATION: Xaa = vitamin B5

<400> SEQUENCE: 29

Xaa Xaa Arg Arg Gln Glu Gln Leu Glu Arg Ala Leu Asn Ser Ser Arg
1               5                   10                  15

Arg Xaa Xaa Xaa
            20

<210> SEQ ID NO 30
<211> LENGTH: 12
<212> TYPE: PRT
<213> ORGANISM: Artificial Sequence
<220> FEATURE:
<223> OTHER INFORMATION: 'Peptide 1' plus vasculature relaxation
      stimulating agent at 3' end;
<220> FEATURE:
<221> NAME/KEY: VARIANT
<222> LOCATION: 12
<223> OTHER INFORMATION: Xaa = R(arginine) or citrulline, or choline at
      3'-end
```

<400> SEQUENCE: 30

Asn Glu Gln Leu Glu Arg Ala Leu Asn Ser Thr Xaa
1               5                   10

<210> SEQ ID NO 31
<211> LENGTH: 13
<212> TYPE: PRT
<213> ORGANISM: Artificial Sequence
<220> FEATURE:
<223> OTHER INFORMATION: 'Peptide 1' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) if Xaa(13) = R, or Xaa =
      citrulline if Xaa(13) = citrullien, or Xaa = choline if Xaa(13) =
      vitamin B5 at 3'end
<220> FEATURE:
<221> NAME/KEY: VARIANT
<222> LOCATION: 13
<223> OTHER INFORMATION: Xaa = R(arginine) if Xaa(12) = R, or Xaa =
      citrulline if Xaa(12) = citrulline, or Xaa = vitamin B5 if
      Xaa(12) = choline at 3'-end

<400> SEQUENCE: 31

Asn Glu Gln Leu Glu Arg Ala Leu Asn Ser Thr Xaa Xaa
1               5                   10

<210> SEQ ID NO 32
<211> LENGTH: 14
<212> TYPE: PRT
<213> ORGANISM: Artificial Sequence
<220> FEATURE:
<223> OTHER INFORMATION: 'Peptide 1' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) at 3'-end
<220> FEATURE:
<221> NAME/KEY: VARIANT
<222> LOCATION: 13
<223> OTHER INFORMATION: Xaa = R(arginine); or Xaa = choline if
      Xaa(14) = Vitamin B5 at 3'-end
<220> FEATURE:
<221> NAME/KEY: VARIANT
<222> LOCATION: 14
<223> OTHER INFORMATION: Xaa = R(arginine) or citrulline or cholin or
      vitamin B5 at 3'-end

<400> SEQUENCE: 32

Asn Glu Gln Leu Glu Arg Ala Leu Asn Ser Thr Xaa Xaa Xaa
1               5                   10

<210> SEQ ID NO 33
<211> LENGTH: 15
<212> TYPE: PRT
<213> ORGANISM: Artificial Sequence
<220> FEATURE:
<223> OTHER INFORMATION: 'Peptide 1' plus vasculature relaxation
      stimulating agents at 3' end;
<220> FEATURE:
<221> NAME/KEY: VARIANT
<222> LOCATION: 12
<223> OTHER INFORMATION: Xaa = R (arginine) at 3'-end
<220> FEATURE:
<221> NAME/KEY: VARIANT
<222> LOCATION: 13
<223> OTHER INFORMATION: Xaa = R (arginine) at 3'-end
<220> FEATURE:
<221> NAME/KEY: VARIANT
<222> LOCATION: 14

```
<223> OTHER INFORMATION: Xaa = citrulline or choline-vitamin B5 at
      3'-end
<220> FEATURE:
<221> NAME/KEY: VARIANT
<222> LOCATION: 15
<223> OTHER INFORMATION: Xaa = citrulline at 3'-end if Xaa(14) is not
      choline

<400> SEQUENCE: 33

Asn Glu Gln Leu Glu Arg Ala Leu Asn Ser Thr Xaa Xaa Xaa Xaa
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: 'Peptide 1' plus vasculature relaxation
      stimulating agents (here: arginine) at 5'- and 3' end;

<400> SEQUENCE: 34

Arg Asn Glu Gln Leu Glu Arg Ala Leu Asn Ser Thr Arg
1               5                   10

<210> SEQ ID NO 35
<211> LENGTH: 15
<212> TYPE: PRT
<213> ORGANISM: Artificial Sequence
<220> FEATURE:
<223> OTHER INFORMATION: 'Peptide 1' plus vasculature relaxation
      stimulating agents at 5'- and 3' end;

<400> SEQUENCE: 35

Arg Arg Asn Glu Gln Leu Glu Arg Ala Leu Asn Ser Thr Arg Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: 'Peptide 1' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline
<220> FEATURE:
<221> NAME/KEY: VARIANT
<222> LOCATION: 15
<223> OTHER INFORMATION: Xaa = citrulline

<400> SEQUENCE: 36

Xaa Arg Asn Glu Gln Leu Glu Arg Ala Leu Asn Ser Thr Arg Xaa
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: 'Peptide 1' plus vasculature relaxation
      stimulating agents at 5'- and 3' end;
<220> FEATURE:
<221> NAME/KEY: VARIANT
<222> LOCATION: 16
<223> OTHER INFORMATION: Xaa = choline or choline-vitamin B5

<400> SEQUENCE: 37

Arg Arg Asn Glu Gln Leu Glu Arg Ala Leu Asn Ser Thr Arg Arg Xaa
```

```
<210> SEQ ID NO 38
<211> LENGTH: 19
<212> TYPE: PRT
<213> ORGANISM: Artificial Sequence
<220> FEATURE:
<223> OTHER INFORMATION: 'Peptide 1' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5' end
<220> FEATURE:
<221> NAME/KEY: VARIANT
<222> LOCATION: 2
<223> OTHER INFORMATION: Xaa = citrulline at 5' end
<220> FEATURE:
<221> NAME/KEY: VARIANT
<222> LOCATION: 18
<223> OTHER INFORMATION: Xaa = citrulline at 3' end
<220> FEATURE:
<221> NAME/KEY: VARIANT
<222> LOCATION: 19
<223> OTHER INFORMATION: Xaa = citrulline at 3' end

<400> SEQUENCE: 38

Xaa Xaa Arg Arg Asn Glu Gln Leu Glu Arg Ala Leu Asn Ser Thr Arg
1               5                   10                  15

Arg Xaa Xaa

<210> SEQ ID NO 39
<211> LENGTH: 20
<212> TYPE: PRT
<213> ORGANISM: Artificial Sequence
<220> FEATURE:
<223> OTHER INFORMATION: 'Peptide 1' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5'-end
<220> FEATURE:
<221> NAME/KEY: VARIANT
<222> LOCATION: 2
<223> OTHER INFORMATION: Xaa = citrulline at 5'-end
<220> FEATURE:
<221> NAME/KEY: VARIANT
<222> LOCATION: 18
<223> OTHER INFORMATION: Xaa = citrulline at 3'-end
<220> FEATURE:
<221> NAME/KEY: VARIANT
<222> LOCATION: 19
<223> OTHER INFORMATION: Xaa = citrulline at 3'-end
<220> FEATURE:
<221> NAME/KEY: VARIANT
<222> LOCATION: 20
<223> OTHER INFORMATION: Xaa = vitamin B5

<400> SEQUENCE: 39

Xaa Xaa Arg Arg Asn Glu Gln Leu Glu Arg Ala Leu Asn Ser Thr Arg
1               5                   10                  15

Arg Xaa Xaa Xaa
            20

<210> SEQ ID NO 40
<211> LENGTH: 12
<212> TYPE: PRT
<213> ORGANISM: Artificial Sequence
<220> FEATURE:
<223> OTHER INFORMATION: 'Peptide 2' plus vasculature relaxation
      stimulating agent at 3' end;
```

-continued

```
<220> FEATURE:
<221> NAME/KEY: VARIANT
<222> LOCATION: 12
<223> OTHER INFORMATION: Xaa = R(arginine) or citrulline, or choline at
      3'-end

<400> SEQUENCE: 40

Asn Glu Gln Leu Glu Arg Ala Leu Asn Thr Ser Xaa
1               5                   10

<210> SEQ ID NO 41
<211> LENGTH: 13
<212> TYPE: PRT
<213> ORGANISM: Artificial Sequence
<220> FEATURE:
<223> OTHER INFORMATION: 'Peptide 2' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) if Xaa(13) = R; or Xaa =
      citrulline if Xaa(13) = citrulline; or Xaa = choline if Xaa(13) =
      vitamin B5 at 3'-end
<220> FEATURE:
<221> NAME/KEY: VARIANT
<222> LOCATION: 13
<223> OTHER INFORMATION: Xaa = R(arginine) if Xaa(12) = R, or Xaa =
      citrulline if Xaa(12) = citrulline, or Xaa = vitamin B5 if
      Xaa(12) = choline at 3'-end

<400> SEQUENCE: 41

Asn Glu Gln Leu Glu Arg Ala Leu Asn Thr Ser Xaa Xaa
1               5                   10

<210> SEQ ID NO 42
<211> LENGTH: 14
<212> TYPE: PRT
<213> ORGANISM: Artificial Sequence
<220> FEATURE:
<223> OTHER INFORMATION: 'Peptide 2' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) at 3'-end
<220> FEATURE:
<221> NAME/KEY: VARIANT
<222> LOCATION: 13
<223> OTHER INFORMATION: Xaa = R(arginine); or Xaa = choline if
      Xaa(14) = Vitamin B5 at 3'-end
<220> FEATURE:
<221> NAME/KEY: VARIANT
<222> LOCATION: 14
<223> OTHER INFORMATION: Xaa = R(arginine) or citrulline or cholin or
      vitamin B5 at 3'-end

<400> SEQUENCE: 42

Asn Glu Gln Leu Glu Arg Ala Leu Asn Thr Ser Xaa Xaa Xaa
1               5                   10

<210> SEQ ID NO 43
<211> LENGTH: 15
<212> TYPE: PRT
<213> ORGANISM: Artificial Sequence
<220> FEATURE:
<223> OTHER INFORMATION: 'Peptide 2' plus vasculature relaxation
      stimulating agents at 3' end;
<220> FEATURE:
<221> NAME/KEY: VARIANT
<222> LOCATION: 12
<223> OTHER INFORMATION: Xaa = R (arginine) at 3'-end
<220> FEATURE:
<221> NAME/KEY: VARIANT
```

```
<222> LOCATION: 13
<223> OTHER INFORMATION: Xaa = R (arginine) at 3'-end
<220> FEATURE:
<221> NAME/KEY: VARIANT
<222> LOCATION: 14
<223> OTHER INFORMATION: Xaa = citrulline or choline-vitamin B5 at
      3'-end
<220> FEATURE:
<221> NAME/KEY: VARIANT
<222> LOCATION: 15
<223> OTHER INFORMATION: Xaa = citrulline at 3'-end if Xaa(14) is not
      choline

<400> SEQUENCE: 43

Asn Glu Gln Leu Glu Arg Ala Leu Asn Thr Ser Xaa Xaa Xaa Xaa
1               5                   10                  15

<210> SEQ ID NO 44
<211> LENGTH: 13
<212> TYPE: PRT
<213> ORGANISM: Artificial Sequence
<220> FEATURE:
<223> OTHER INFORMATION: 'Peptide 2' plus vasculature relaxation
      stimulating agents (here: arginine) at 5'- and 3' end;

<400> SEQUENCE: 44

Arg Asn Glu Gln Leu Glu Arg Ala Leu Asn Thr Ser Arg
1               5                   10

<210> SEQ ID NO 45
<211> LENGTH: 15
<212> TYPE: PRT
<213> ORGANISM: Artificial Sequence
<220> FEATURE:
<223> OTHER INFORMATION: 'Peptide 2' plus vasculature relaxation
      stimulating agents at 5'- and 3' end;

<400> SEQUENCE: 45

Arg Arg Asn Glu Gln Leu Glu Arg Ala Leu Asn Thr Ser Arg Arg
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: 'Peptide 2' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline
<220> FEATURE:
<221> NAME/KEY: VARIANT
<222> LOCATION: 15
<223> OTHER INFORMATION: Xaa = citrulline

<400> SEQUENCE: 46

Xaa Arg Asn Glu Gln Leu Glu Arg Ala Leu Asn Thr Ser Arg Xaa
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: 'Peptide 2' plus vasculature relaxation
      stimulating agents at 5'- and 3' end;
<220> FEATURE:
<221> NAME/KEY: VARIANT
<222> LOCATION: 16
```

```
<223> OTHER INFORMATION: Xaa = choline or choline-vitamin B5

<400> SEQUENCE: 47

Arg Arg Asn Glu Gln Leu Glu Arg Ala Leu Asn Thr Ser Arg Arg Xaa
1               5                   10                  15

<210> SEQ ID NO 48
<211> LENGTH: 19
<212> TYPE: PRT
<213> ORGANISM: Artificial Sequence
<220> FEATURE:
<223> OTHER INFORMATION: 'Peptide 2' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5' end
<220> FEATURE:
<221> NAME/KEY: VARIANT
<222> LOCATION: 2
<223> OTHER INFORMATION: Xaa = citrulline at 5' end
<220> FEATURE:
<221> NAME/KEY: VARIANT
<222> LOCATION: 18
<223> OTHER INFORMATION: Xaa = citrulline at 3' end
<220> FEATURE:
<221> NAME/KEY: VARIANT
<222> LOCATION: 19
<223> OTHER INFORMATION: Xaa = citrulline at 3' end

<400> SEQUENCE: 48

Xaa Xaa Arg Arg Asn Glu Gln Leu Glu Arg Ala Leu Asn Thr Ser Arg
1               5                   10                  15

Arg Xaa Xaa

<210> SEQ ID NO 49
<211> LENGTH: 20
<212> TYPE: PRT
<213> ORGANISM: Artificial Sequence
<220> FEATURE:
<223> OTHER INFORMATION: 'Peptide 2' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5'-end
<220> FEATURE:
<221> NAME/KEY: VARIANT
<222> LOCATION: 2
<223> OTHER INFORMATION: Xaa = citrulline at 5'-end
<220> FEATURE:
<221> NAME/KEY: VARIANT
<222> LOCATION: 18
<223> OTHER INFORMATION: Xaa = citrulline at 3'-end
<220> FEATURE:
<221> NAME/KEY: VARIANT
<222> LOCATION: 19
<223> OTHER INFORMATION: Xaa = citrulline at 3'-end
<220> FEATURE:
<221> NAME/KEY: VARIANT
<222> LOCATION: 20
<223> OTHER INFORMATION: Xaa = vitamin B5

<400> SEQUENCE: 49

Xaa Xaa Arg Arg Asn Glu Gln Leu Glu Arg Ala Leu Asn Thr Ser Arg
1               5                   10                  15

Arg Xaa Xaa Xaa
            20

<210> SEQ ID NO 50
<211> LENGTH: 12
```

```
<212> TYPE: PRT
<213> ORGANISM: Artificial Sequence
<220> FEATURE:
<223> OTHER INFORMATION: 'Peptide 3' plus vasculature relaxation
      stimulating agent at 3' end;
<220> FEATURE:
<221> NAME/KEY: VARIANT
<222> LOCATION: 12
<223> OTHER INFORMATION: Xaa = R(arginine) or citrulline, or choline at
      3'-end

<400> SEQUENCE: 50

Gln Asp Gln Leu Glu Arg Ala Leu Asn Ser Thr Xaa
1               5                   10

<210> SEQ ID NO 51
<211> LENGTH: 13
<212> TYPE: PRT
<213> ORGANISM: Artificial Sequence
<220> FEATURE:
<223> OTHER INFORMATION: 'Peptide 3' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) if Xaa(13) = R; or Xaa =
      citrulline if Xaa(13) = citrulline; or Xaa = choline if Xaa(13) =
      vitamin B5 at 3'-end
<220> FEATURE:
<221> NAME/KEY: VARIANT
<222> LOCATION: 13
<223> OTHER INFORMATION: Xaa = R(arginine) if Xaa(12) = R, or Xaa =
      citrulline if Xaa(12) = citrulline, or Xaa = vitamin B5 if
      Xaa(12) = choline at 3'-end

<400> SEQUENCE: 51

Gln Asp Gln Leu Glu Arg Ala Leu Asn Ser Thr Xaa Xaa
1               5                   10

<210> SEQ ID NO 52
<211> LENGTH: 14
<212> TYPE: PRT
<213> ORGANISM: Artificial Sequence
<220> FEATURE:
<223> OTHER INFORMATION: 'Peptide 3' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) at 3'-end
<220> FEATURE:
<221> NAME/KEY: VARIANT
<222> LOCATION: 13
<223> OTHER INFORMATION: Xaa = R(arginine); or Xaa = choline if
      Xaa(14) = Vitamin B5 at 3'-end
<220> FEATURE:
<221> NAME/KEY: VARIANT
<222> LOCATION: 14
<223> OTHER INFORMATION: Xaa = R(arginine) or citrulline or cholin or
      vitamin B5 at 3'-end

<400> SEQUENCE: 52

Gln Asp Gln Leu Glu Arg Ala Leu Asn Ser Thr Xaa Xaa Xaa
1               5                   10

<210> SEQ ID NO 53
<211> LENGTH: 15
<212> TYPE: PRT
<213> ORGANISM: Artificial Sequence
<220> FEATURE:
<223> OTHER INFORMATION: 'Peptide 3' plus vasculature relaxation
      stimulating agents at 3' end;
<220> FEATURE:
```

```
<221> NAME/KEY: VARIANT
<222> LOCATION: 12
<223> OTHER INFORMATION: Xaa = R (arginine) at 3'-end
<220> FEATURE:
<221> NAME/KEY: VARIANT
<222> LOCATION: 13
<223> OTHER INFORMATION: Xaa = R (arginine) at 3'-end
<220> FEATURE:
<221> NAME/KEY: VARIANT
<222> LOCATION: 14
<223> OTHER INFORMATION: Xaa = citrulline or choline-vitamin B5 at
      3'-end
<220> FEATURE:
<221> NAME/KEY: VARIANT
<222> LOCATION: 15
<223> OTHER INFORMATION: Xaa = citrulline at 3'-end if Xaa(14) is not
      choline

<400> SEQUENCE: 53

Gln Asp Gln Leu Glu Arg Ala Leu Asn Ser Thr Xaa Xaa Xaa Xaa
1               5                   10                  15

<210> SEQ ID NO 54
<211> LENGTH: 13
<212> TYPE: PRT
<213> ORGANISM: Artificial Sequence
<220> FEATURE:
<223> OTHER INFORMATION: 'Peptide 3' plus vasculature relaxation
      stimulating agents (here: arginine) at 5'- and 3' end;

<400> SEQUENCE: 54

Arg Gln Asp Gln Leu Glu Arg Ala Leu Asn Ser Thr Arg
1               5                   10

<210> SEQ ID NO 55
<211> LENGTH: 15
<212> TYPE: PRT
<213> ORGANISM: Artificial Sequence
<220> FEATURE:
<223> OTHER INFORMATION: 'Peptide 3' plus vasculature relaxation
      stimulating agents at 5'- and 3' end;

<400> SEQUENCE: 55

Arg Arg Gln Asp Gln Leu Glu Arg Ala Leu Asn Ser Thr Arg Arg
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: 'Peptide 3' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline
<220> FEATURE:
<221> NAME/KEY: VARIANT
<222> LOCATION: 15
<223> OTHER INFORMATION: Xaa = citrulline

<400> SEQUENCE: 56

Xaa Arg Gln Asp Gln Leu Glu Arg Ala Leu Asn Ser Thr Arg Xaa
1               5                   10                  15

<210> SEQ ID NO 57
<211> LENGTH: 16
<212> TYPE: PRT
<213> ORGANISM: Artificial Sequence
<220> FEATURE:
```

-continued

```
<223> OTHER INFORMATION: 'Peptide 3' plus vasculature relaxation
      stimulating agents at 5'- and 3' end;
<220> FEATURE:
<221> NAME/KEY: VARIANT
<222> LOCATION: 16
<223> OTHER INFORMATION: Xaa = choline or choline-vitamin B5

<400> SEQUENCE: 57

Arg Arg Gln Asp Gln Leu Glu Arg Ala Leu Asn Ser Thr Arg Arg Xaa
1               5                   10                  15

<210> SEQ ID NO 58
<211> LENGTH: 19
<212> TYPE: PRT
<213> ORGANISM: Artificial Sequence
<220> FEATURE:
<223> OTHER INFORMATION: 'Peptide 3' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5' end
<220> FEATURE:
<221> NAME/KEY: VARIANT
<222> LOCATION: 2
<223> OTHER INFORMATION: Xaa = citrulline at 5' end
<220> FEATURE:
<221> NAME/KEY: VARIANT
<222> LOCATION: 18
<223> OTHER INFORMATION: Xaa = citrulline at 3' end
<220> FEATURE:
<221> NAME/KEY: VARIANT
<222> LOCATION: 19
<223> OTHER INFORMATION: Xaa = citrulline at 3' end

<400> SEQUENCE: 58

Xaa Xaa Arg Arg Gln Asp Gln Leu Glu Arg Ala Leu Asn Ser Thr Arg
1               5                   10                  15

Arg Xaa Xaa

<210> SEQ ID NO 59
<211> LENGTH: 20
<212> TYPE: PRT
<213> ORGANISM: Artificial Sequence
<220> FEATURE:
<223> OTHER INFORMATION: 'Peptide 3' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5'-end
<220> FEATURE:
<221> NAME/KEY: VARIANT
<222> LOCATION: 2
<223> OTHER INFORMATION: Xaa = citrulline at 5'-end
<220> FEATURE:
<221> NAME/KEY: VARIANT
<222> LOCATION: 18
<223> OTHER INFORMATION: Xaa = citrulline at 3'-end
<220> FEATURE:
<221> NAME/KEY: VARIANT
<222> LOCATION: 19
<223> OTHER INFORMATION: Xaa = citrulline at 3'-end
<220> FEATURE:
<221> NAME/KEY: VARIANT
<222> LOCATION: 20
<223> OTHER INFORMATION: Xaa = vitamin B5

<400> SEQUENCE: 59

Xaa Xaa Arg Arg Gln Asp Gln Leu Glu Arg Ala Leu Asn Ser Thr Arg
1               5                   10                  15

Arg Xaa Xaa Xaa
```

-continued

```
                        20

<210> SEQ ID NO 60
<211> LENGTH: 12
<212> TYPE: PRT
<213> ORGANISM: Artificial Sequence
<220> FEATURE:
<223> OTHER INFORMATION: 'Peptide 4' plus vasculature relaxation
      stimulating agent at 3' end;
<220> FEATURE:
<221> NAME/KEY: VARIANT
<222> LOCATION: 12
<223> OTHER INFORMATION: Xaa = R(arginine) or citrulline, or choline at
      3'-end

<400> SEQUENCE: 60

Gln Asp Gln Leu Glu Arg Ala Leu Asn Thr Ser Xaa
1               5                   10

<210> SEQ ID NO 61
<211> LENGTH: 13
<212> TYPE: PRT
<213> ORGANISM: Artificial Sequence
<220> FEATURE:
<223> OTHER INFORMATION: 'Peptide 4' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) if Xaa(13) = R; or Xaa =
      citrulline if Xaa(13) = citrulline; or Xaa = choline if Xaa(13) =
      vitamin B5 at 3'-end
<220> FEATURE:
<221> NAME/KEY: VARIANT
<222> LOCATION: 13
<223> OTHER INFORMATION: Xaa = R(arginine) if Xaa(12) = R, or Xaa =
      citrulline if Xaa(12) = citrulline, or Xaa = vitamin B5 if
      Xaa(12) = choline at 3'-end

<400> SEQUENCE: 61

Gln Asp Gln Leu Glu Arg Ala Leu Asn Thr Ser Xaa Xaa
1               5                   10

<210> SEQ ID NO 62
<211> LENGTH: 14
<212> TYPE: PRT
<213> ORGANISM: Artificial Sequence
<220> FEATURE:
<223> OTHER INFORMATION: 'Peptide 4' plus vasculature relaxation
      stimulating agents at 3' end;
<220> FEATURE:
<221> NAME/KEY: VARIANT
<222> LOCATION: 12
<223> OTHER INFORMATION: Xaa = R(arginine) at 3'-end
<220> FEATURE:
<221> NAME/KEY: VARIANT
<222> LOCATION: 13
<223> OTHER INFORMATION: Xaa = R(arginine); or Xaa = choline if
      Xaa(14) = Vitamin B5 at 3'-end
<220> FEATURE:
<221> NAME/KEY: VARIANT
<222> LOCATION: 14
<223> OTHER INFORMATION: Xaa = R(arginine) or citrulline or cholin or
      vitamin B5 at 3'-end

<400> SEQUENCE: 62

Gln Asp Gln Leu Glu Arg Ala Leu Asn Thr Ser Xaa Xaa Xaa
1               5                   10

<210> SEQ ID NO 63
<211> LENGTH: 15
<212> TYPE: PRT
```

```
<213> ORGANISM: Artificial Sequence
<220> FEATURE:
<223> OTHER INFORMATION: 'Peptide 4' plus vasculature relaxation
      stimulating agents at 3' end;
<220> FEATURE:
<221> NAME/KEY: VARIANT
<222> LOCATION: 12
<223> OTHER INFORMATION: Xaa = R (arginine) at 3'-end
<220> FEATURE:
<221> NAME/KEY: VARIANT
<222> LOCATION: 13
<223> OTHER INFORMATION: Xaa = R (arginine) at 3'-end
<220> FEATURE:
<221> NAME/KEY: VARIANT
<222> LOCATION: 14
<223> OTHER INFORMATION: Xaa = citrulline or choline-vitamin B5 at
      3'-end
<220> FEATURE:
<221> NAME/KEY: VARIANT
<222> LOCATION: 15
<223> OTHER INFORMATION: Xaa = citrulline at 3'-end if Xaa(14) is not
      choline

<400> SEQUENCE: 63

Gln Asp Gln Leu Glu Arg Ala Leu Asn Thr Ser Xaa Xaa Xaa Xaa
1               5                   10                  15

<210> SEQ ID NO 64
<211> LENGTH: 13
<212> TYPE: PRT
<213> ORGANISM: Artificial Sequence
<220> FEATURE:
<223> OTHER INFORMATION: 'Peptide 4' plus vasculature relaxation
      stimulating agents (here: arginine) at 5'- and 3' end;

<400> SEQUENCE: 64

Arg Gln Asp Gln Leu Glu Arg Ala Leu Asn Thr Ser Arg
1               5                   10

<210> SEQ ID NO 65
<211> LENGTH: 15
<212> TYPE: PRT
<213> ORGANISM: Artificial Sequence
<220> FEATURE:
<223> OTHER INFORMATION: 'Peptide 4' plus vasculature relaxation
      stimulating agents at 5'- and 3' end;

<400> SEQUENCE: 65

Arg Arg Gln Asp Gln Leu Glu Arg Ala Leu Asn Thr Ser Arg Arg
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: 'Peptide 4' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline
<220> FEATURE:
<221> NAME/KEY: VARIANT
<222> LOCATION: 15
<223> OTHER INFORMATION: Xaa = citrulline

<400> SEQUENCE: 66

Xaa Arg Gln Asp Gln Leu Glu Arg Ala Leu Asn Thr Ser Arg Xaa
1               5                   10                  15
```

```
<210> SEQ ID NO 67
<211> LENGTH: 16
<212> TYPE: PRT
<213> ORGANISM: Artificial Sequence
<220> FEATURE:
<223> OTHER INFORMATION: 'Peptide 4' plus vasculature relaxation
      stimulating agents at 5'- and 3' end;
<220> FEATURE:
<221> NAME/KEY: VARIANT
<222> LOCATION: 16
<223> OTHER INFORMATION: Xaa = choline or choline-vitamin B5

<400> SEQUENCE: 67

Arg Arg Gln Asp Gln Leu Glu Arg Ala Leu Asn Thr Ser Arg Arg Xaa
1               5                   10                  15

<210> SEQ ID NO 68
<211> LENGTH: 19
<212> TYPE: PRT
<213> ORGANISM: Artificial Sequence
<220> FEATURE:
<223> OTHER INFORMATION: 'Peptide 4' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5' end
<220> FEATURE:
<221> NAME/KEY: VARIANT
<222> LOCATION: 2
<223> OTHER INFORMATION: Xaa = citrulline at 5' end
<220> FEATURE:
<221> NAME/KEY: VARIANT
<222> LOCATION: 18
<223> OTHER INFORMATION: Xaa = citrulline at 3' end
<220> FEATURE:
<221> NAME/KEY: VARIANT
<222> LOCATION: 19
<223> OTHER INFORMATION: Xaa = citrulline at 3' end

<400> SEQUENCE: 68

Xaa Xaa Arg Arg Gln Asp Gln Leu Glu Arg Ala Leu Asn Thr Ser Arg
1               5                   10                  15

Arg Xaa Xaa

<210> SEQ ID NO 69
<211> LENGTH: 20
<212> TYPE: PRT
<213> ORGANISM: Artificial Sequence
<220> FEATURE:
<223> OTHER INFORMATION: 'Peptide 4' plus vasculature relaxation
      stimulating agents at 5'- and 3' end;
<220> FEATURE:
<221> NAME/KEY: VARIANT
<222> LOCATION: 1
<223> OTHER INFORMATION: Xaa = citrulline at 5'-end
<220> FEATURE:
<221> NAME/KEY: VARIANT
<222> LOCATION: 2
<223> OTHER INFORMATION: Xaa = citrulline at 5'-end
<220> FEATURE:
<221> NAME/KEY: VARIANT
<222> LOCATION: 18
<223> OTHER INFORMATION: Xaa = citrulline at 3'-end
<220> FEATURE:
<221> NAME/KEY: VARIANT
<222> LOCATION: 19
<223> OTHER INFORMATION: Xaa = citrulline at 3'-end
<220> FEATURE:
<221> NAME/KEY: VARIANT
<222> LOCATION: 20
<223> OTHER INFORMATION: Xaa = vitamin B5

<400> SEQUENCE: 69
```

```
Xaa Xaa Arg Arg Gln Asp Gln Leu Glu Arg Ala Leu Asn Thr Ser Arg
1               5                   10                  15

Arg Xaa Xaa Xaa
            20

<210> SEQ ID NO 70
<211> LENGTH: 12
<212> TYPE: PRT
<213> ORGANISM: Artificial Sequence
<220> FEATURE:
<223> OTHER INFORMATION: 'Peptide 0' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5

<400> SEQUENCE: 70

Xaa Gln Glu Gln Leu Glu Arg Ala Leu Asn Ser Ser
1               5                   10

<210> SEQ ID NO 71
<211> LENGTH: 13
<212> TYPE: PRT
<213> ORGANISM: Artificial Sequence
<220> FEATURE:
<223> OTHER INFORMATION: 'Peptide 1' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5

<400> SEQUENCE: 71

Xaa Asn Glu Gln Leu Glu Arg Ala Leu Asn Ser Thr Arg
1               5                   10

<210> SEQ ID NO 72
<211> LENGTH: 12
<212> TYPE: PRT
<213> ORGANISM: Artificial Sequence
<220> FEATURE:
<223> OTHER INFORMATION: 'Peptide 2' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5

<400> SEQUENCE: 72

Xaa Asn Glu Gln Leu Glu Arg Ala Leu Asn Thr Ser
1               5                   10

<210> SEQ ID NO 73
<211> LENGTH: 12
<212> TYPE: PRT
<213> ORGANISM: Artificial Sequence
<220> FEATURE:
<223> OTHER INFORMATION: 'Peptide 3' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5

<400> SEQUENCE: 73
```

```
Xaa Gln Asp Gln Leu Glu Arg Ala Leu Asn Ser Thr
1               5                   10

<210> SEQ ID NO 74
<211> LENGTH: 12
<212> TYPE: PRT
<213> ORGANISM: Artificial Sequence
<220> FEATURE:
<223> OTHER INFORMATION: 'Peptide 4' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5

<400> SEQUENCE: 74

Xaa Gln Asp Gln Leu Glu Arg Ala Leu Asn Thr Ser
1               5                   10

<210> SEQ ID NO 75
<211> LENGTH: 13
<212> TYPE: PRT
<213> ORGANISM: Artificial Sequence
<220> FEATURE:
<223> OTHER INFORMATION: 'Peptide 0' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5

<400> SEQUENCE: 75

Xaa Xaa Gln Glu Gln Leu Glu Arg Ala Leu Asn Ser Ser
1               5                   10

<210> SEQ ID NO 76
<211> LENGTH: 13
<212> TYPE: PRT
<213> ORGANISM: Artificial Sequence
<220> FEATURE:
<223> OTHER INFORMATION: 'Peptide 1' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5

<400> SEQUENCE: 76

Xaa Xaa Asn Glu Gln Leu Glu Arg Ala Leu Asn Ser Thr
1               5                   10

<210> SEQ ID NO 77
<211> LENGTH: 13
<212> TYPE: PRT
<213> ORGANISM: Artificial Sequence
<220> FEATURE:
```

```
<223> OTHER INFORMATION: 'Peptide 2' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5

<400> SEQUENCE: 77

Xaa Xaa Asn Glu Gln Leu Glu Arg Ala Leu Asn Thr Ser
1               5                   10

<210> SEQ ID NO 78
<211> LENGTH: 13
<212> TYPE: PRT
<213> ORGANISM: Artificial Sequence
<220> FEATURE:
<223> OTHER INFORMATION: 'Peptide 3' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5

<400> SEQUENCE: 78

Xaa Xaa Gln Asp Gln Leu Glu Arg Ala Leu Asn Ser Thr
1               5                   10

<210> SEQ ID NO 79
<211> LENGTH: 13
<212> TYPE: PRT
<213> ORGANISM: Artificial Sequence
<220> FEATURE:
<223> OTHER INFORMATION: 'Peptide 4' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5

<400> SEQUENCE: 79

Xaa Xaa Gln Asp Gln Leu Glu Arg Ala Leu Asn Thr Ser
1               5                   10

<210> SEQ ID NO 80
<211> LENGTH: 14
<212> TYPE: PRT
<213> ORGANISM: Artificial Sequence
<220> FEATURE:
<223> OTHER INFORMATION: 'Peptide 0' plus vasculature relaxation
      stimulating agents at 5'-end
<220> FEATURE:
<221> NAME/KEY: VARIANT
```

```
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) and Xaa(3) = R, or
      Xaa = citrulline if Xaa(1) and Xaa(3) = citrulline, or Xaa =
      choline if Xaa(1) and Xaa(3) is choline, or Xaa = vitamin B5 if
      Xaa(1) and Xaa(3) is vitamin B5
<220> FEATURE:
<221> NAME/KEY: VARIANT
<222> LOCATION: 3
<223> OTHER INFORMATION: Xaa = R (arginine) if Xaa(1) and Xaa(2) = R, or
      Xaa = citrulline if Xaa(1) and Xaa(2) = citrulline, or Xaa =
      choline if Xaa(1) and Xaa(2) is choline, or Xaa = vitamin B5 if
      Xaa(1) and Xaa(2) is vitamin B5

<400> SEQUENCE: 80

Xaa Xaa Xaa Gln Glu Gln Leu Glu Arg Ala Leu Asn Ser Ser
1               5                   10

<210> SEQ ID NO 81
<211> LENGTH: 14
<212> TYPE: PRT
<213> ORGANISM: Artificial Sequence
<220> FEATURE:
<223> OTHER INFORMATION: 'Peptide 1' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5
<220> FEATURE:
<221> NAME/KEY: VARIANT
<222> LOCATION: 3
<223> OTHER INFORMATION: Xaa = R (arginine) if Xaa(1) and Xaa(2) = R, or
      Xaa = citrulline if Xaa(1) and Xaa(2) = citrulline, or Xaa =
      choline if Xaa(1) and Xaa(2) is choline, or Xaa = vitamin B5 if
      Xaa(1) and Xaa(2) is vitamin B5

<400> SEQUENCE: 81

Xaa Xaa Xaa Asn Glu Gln Leu Glu Arg Ala Leu Asn Ser Thr
1               5                   10

<210> SEQ ID NO 82
<211> LENGTH: 14
<212> TYPE: PRT
<213> ORGANISM: Artificial Sequence
<220> FEATURE:
<223> OTHER INFORMATION: 'Peptide 2' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5
<220> FEATURE:
<221> NAME/KEY: VARIANT
<222> LOCATION: 3
<223> OTHER INFORMATION: Xaa = R (arginine) if Xaa(1) and Xaa(2) = R, or
      Xaa = citrulline if Xaa(1) and Xaa(2) = citrulline, or Xaa =
```

-continued

```
      choline if Xaa(1) and Xaa(2) is choline, or Xaa = vitamin B5 if
      Xaa(1) and Xaa(2) is vitamin B5

<400> SEQUENCE: 82

Xaa Xaa Xaa Asn Glu Gln Leu Glu Arg Ala Leu Asn Thr Ser
1               5                   10

<210> SEQ ID NO 83
<211> LENGTH: 14
<212> TYPE: PRT
<213> ORGANISM: Artificial Sequence
<220> FEATURE:
<223> OTHER INFORMATION: 'Peptide 3' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5
<220> FEATURE:
<221> NAME/KEY: VARIANT
<222> LOCATION: 3
<223> OTHER INFORMATION: Xaa = R (arginine) if Xaa(1) and Xaa(2) = R, or
      Xaa = citrulline if Xaa(1) and Xaa(2) = citrulline, or Xaa =
      choline if Xaa(1) and Xaa(2) is choline, or Xaa = vitamin B5 if
      Xaa(1) and Xaa(2) is vitamin B5

<400> SEQUENCE: 83

Xaa Xaa Xaa Gln Asp Gln Leu Glu Arg Ala Leu Asn Ser Thr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: 'Peptide 4' plus vasculature relaxation
      stimulating agents at 5'-end
<220> FEATURE:
<221> NAME/KEY: VARIANT
<222> LOCATION: 1
<223> OTHER INFORMATION: Xaa = R (arginine) or citrulline or choline or
      vitamin B5
<220> FEATURE:
<221> NAME/KEY: VARIANT
<222> LOCATION: 2
<223> OTHER INFORMATION: Xaa = R (arginine) if Xaa(1) = R, or Xaa =
      citrulline if Xaa(1) = citrulline, or Xaa = choline if Xaa(1) is
      choline, or Xaa = vitamin B5 if Xaa(1) is vitamin B5
<220> FEATURE:
<221> NAME/KEY: VARIANT
<222> LOCATION: 3
<223> OTHER INFORMATION: Xaa = R (arginine) if Xaa(1) and Xaa(2) = R, or
      Xaa = citrulline if Xaa(1) and Xaa(2) = citrulline, or Xaa =
      choline if Xaa(1) and Xaa(2) is choline, or Xaa = vitamin B5 if
      Xaa(1) and Xaa(2) is vitamin B5

<400> SEQUENCE: 84

Xaa Xaa Xaa Gln Asp Gln Leu Glu Arg Ala Leu Asn Thr Ser
1               5                   10
```

COSMETIC FORMULATIONS FOR TOPICAL APPLICATIONS CONTAINING ERYTHROPOIETIN-DERIVED MOLECULES

FIELD OF THE INVENTION

The invention relates to cosmetic formulations and new peptide related entities designed for the cosmetic treatment of the human skin. In more detail, the invention is related to peptides that target CD90 positive tissue cells and correspond to or derive from the partial sequence of erythropoietin (EPO) but do not substantially elicit a hematopoietic but a tissue regenerative and protective effect.

In particular, the invention discloses EPO-derived tissue-protective peptides in functional relation to lipid structures and agents that trigger vasculature relaxation and promote transdermal transport of the polypeptide entities to the targeted skin cells.

BACKGROUND OF THE INVENTION

Cluster Differentiation 90 (CD90) is a cell adhesion molecule and the smallest member of the immunoglobulin superfamily with a molecular weight of 25-35 KDa. CD90 is also known as thymocyte differentiation antigen-1 (Thy-1) and is a glycoprotein anchored to the cell surface via a glycosylphosphatidylinositol (GPI) motif. In humans, CD90 is expressed on stem cells including Mesenchymal Stem Cells (MSCs), Hematopoietic Stem Cells (HSCs) and Keratinocyte Stem Cells (KSCs) and at varying levels on non-lymphoid tissues such as fibroblasts, neurons and activated endothelial cells. Keratinocytes form the predominant cell type in the epidermis, the outermost layer of the skin, constituting 90% of the cells found there. Those keratinocytes found in the basal layer of the skin are referred to as "basal cells" or "basal keratinocytes.

CD90 expressing skin cells are functioning in inflammation and wound healing by synthesizing and releasing growth factors, cytokines and extracellular matrix components to assist in repairing damaged skin tissue. For instance, monocyte CD90 ligand binds to CD90 on activated endothelial cells during inflammation, focusing the immune cell migration to the sites of inflammation, tissue injury and infection.

Erythropoietin (EPO) is a pleiotropic cytokine glycoprotein that was initially identified as a regulator of red blood cell production in response to hypoxia. The mature human 165 amino acid-long EPO protein sequence is presented by SEQ ID NO: 1

```
                                     (SEQ ID NO: 1)
APPRLICDSRVLERYLLEAKEAENITTGCAEHCSLNENITVPDTKVNFYA

WKRMEVGQQAVEVWQGLALLSEAVLRGQALLVNSSQPWEPLQLHVDKAVS

GLRSLTTLLRALGAQKEAISPPDAASAAPLRTITADTFRKLFRVYSNFLR

GKLKLYTGEACRTGDR
``` and consists of four α-helices, forming a compact globular structure. Human recombinant erythropoietin (expressed in mammalian cells) contains three N-linked and one O-linked oligosaccharide chains which together comprise about 40% of the total molecular weight of the glycoprotein. N-linked glycosylation occurs at asparagine residues (Asn) located at positions 24, 38 and 83 whereas O-linked glycosylation occurs at a serine residue (Ser) located at position 126.

According to the classical original understanding, EPO induces haematopoiesis by dimerizing EPO receptor molecules, which leads to the activation of the EPO receptor-associated Janus tyrosine kinase 2 (Jak2) and secondary signaling molecules such as Stat5 (Brines and Cerami, Nat Rev Neurosci, 2005; 6:484-94). Recombinant EPO is widely used for the treatment of anemia of various origins.

EPO also displays tissue protection properties. In the central nervous system, EPO and EPO receptor are expressed by neurons, glial cells and cerebrovasculature endothelium. EPO was shown to be neurotrophic and neuroprotective in vitro and in animal models of neuronal injury associated with trauma, stroke, ischemia, inflammation and epileptic seizures. The beneficial effects of EPO were also demonstrated in clinical studies of stroke, schizophrenia and progressive multiple sclerosis. EPO protects neurons both directly, by preventing apoptosis, and indirectly, by modulating inflammatory processes and stimulating neurogenesis and angiogenesis (Wang et al., Stroke 2004; 35:1732-7).

It has been shown that some of the cytoprotective effects of erythropoietin are mediated through its binding to heterodimers containing the canonical erythropoietin receptor and the common beta receptor, ßcR (Brines et al., Proc Natl Acad Sci USA 2004; 101: 14 907-14 912). Interestingly, carbamylated erythropoietin binds to these heteroreceptors and exerts tissue-protective effects, whereas it does not bind to the classical erythropoietin receptor and does not stimulate erythropoiesis. ßcR is not required for erythropoiesis. It is assumed that ßcR in combination with the EpoR expressed by nonhematopoietic cells constitutes a tissue-protective receptor, thus creating a tissue-protective heteroreceptor.

A tissue regenerative and wound healing promoting effect of EPO in skin and other tissues was demonstrated numerous times in vivo and in vitro by systemic and even topical application forms (e.g.: Giri et al, Drug Design, Development and Therapy 2015:9; Günter et al., J Transplant Ste Cell Biol 2(1): 4, 2015; Hamed et al., Wound Rep Reg (2014) 22 23-33; WO 2004/001023; WO 2005/063965; WO 2009/083203).

However, with respect to the regeneration of skin defects and injuries, some problems have become evident that restrict the usability of EPO and its analogs to a direct application of such compounds to the defected or injured skin wounds since these polypeptides do not penetrate the skin. Unless applied by intravenously, subcutaneously or by intramuscular injection, the protein erythropoietin or analogous cannot enter the body.

Topical application of EPO alone to the skin will fail, because it lacks skin permeability on its own. This severely limits the applicability of the molecule. Even in these cases it is controversial whether the systemic application has a regenerative potential at all but rather supports the conventional proliferation and maturation of blood cells, and not topical intact skin or tissue regeneration. It is reported that even the subcutaneous injection of 300 Units EPO/kg body weight used were not able to induce skin regeneration.

In addition, wounds are rich in proteinases known to inactivate EPO within minutes, so EPO has a limited potential to be applied topically to enhance wound regeneration due to EPO's short half-life caused by rapid proteolytic degradation. The same can be said with EPO-fragments or variants or derivatives which known in the art. Some of these EPO derivatives or fragments or variants are known to be effective in tissue protection (see, for example, EP 2 933 264, EP 2 371 855, WO 2007/019545).

The restricted availability of these EPO derived polypeptides is a dilemma especially in a situation of skin conditions that are present in aged skin, scar rich tissue or even inflammatory conditions such as neurodermitis or eczema, where even the most superficial areas of the skin are relatively intact. Not even a cosmetic activity of EPO and its analogues would be achievable.

The aim of this invention is to establish and improve applicability of EPO and EPO fragments, analogs, mimetics, variants and derivatives, to skin cells in a close geometric distance rather than a gradient and time of impact manner.

Therefore, in order to overcome the above-specified limitations, the development of new chemical entities is needed that show tissue-protective properties and are able to efficiently target competent cells in skin tissue which trigger and carry out the physiological and biological functions of skin cells to withdraw or to attenuate the damages of the skin caused, for example, by skin aging and outer and inner influences on skin cells based on pathological events.

SUMMARY OF THE INVENTION

This goal is achieved by providing new chemical entities comprising skin tissue-protective EPO analogs or variants lacking erythropoietic activity and being able to target CD90 positive and other competent cells in skin tissue. These novel chemical entities are precisely tailored to be functionally effective in the local microenvironment of the skin cell and can be administered by topical cosmetic administration to the skin.

In a first aspect of the invention, a cosmetic formulation or composition for topical administration to the skin is provided comprising:
(i) a tissue-protective polypeptide (tpP) consisting of not more than 40 and not less than 7, preferably 10-40, more preferably 10-30 amino acids, wherein the tissue-protective peptide is
  an agonist of the EPO receptor (EpoR) and/or the common ß receptor (ßcR) such as an erythropoietin (EPO) peptide fragment, an EPO peptide variant, a peptide derived from an EPO analog or an EPO mimetic, or a peptide composed of amino acid residues which are involved in the binding to EpoR and/or ßcR,
  targets CD90 expressing skin cells, and
  does not or not essentially elicit hematopoietic/erythropoietic efficacy, and
(ii) a lipid compound or a lipid structure, preferably at least a sphingolipid and/or phospholipid, such as a ceramide or a phosphatidylcholine, wherein the tissue-protective polypeptide (tpP) is linked or associated to the lipid compound or lipid structure by mixture, ionic interaction, by covalent bonding, or is embedded or encapsulated therein by forming a micelle or liposomal structure.

In a preferred embodiment of the invention, the cosmetic formulation or composition comprises additionally an agent that triggers vasculature relaxation and/or promotes transport of the tissue-protective polypeptide to the receptor cells. For example, the triggering agent stimulates nitric oxide (NO) and/or acetylcholine formation in the CD90 expressing skin cell. The triggering agent may be directly linked to the tissue-protective polypeptide according to the invention by covalent bonding, thus forming a conjugate molecule as specified in more detail below.

It was found that the lipid structure combined with said tissue protective polypeptides and optionally with the triggering agents and related compounds according to the invention forms, without be bound to this theory, a kind of transporter molecule complex having specific properties which do not have only the properties of the single components. The lipid-peptide-triggering agent molecule-complex in this formulation according to the invention obviously transports the respective effective compounds much better into the microenvironment of the respective skin cells, e.g. CD90 positive skin cells, than standard cosmetic base formulations of the art.

Moreover, it could be shown that the the tissue-protective polypeptide (tpP) in combination with said triggering agent is more effective in the lipid formulation of the invention with respect to tissue protection and anti-inflammation than in the same formulation without its presence (about 2-3 fold). Thus, the triggering agent, preferably in combination with a sphingolipid or phospholipid structure elicits a positive and enhancing effect in this context, and enables a reduction of the dose of the tissue-protective polypeptide according to the invention. Undesired side-effects caused by the polypeptides according to the invention can be minimized.

As already mentioned, the tissue-protective polypeptide (tpP) in this formulation or composition is linked to the triggering/relaxing agent as specified, preferably by covalent bond at the N-terminus and/or at the C-terminus of this polypeptide, thereby forming a conjugate molecule which shows enhanced tissue-protective efficacy. In such close vicinity to the triggering/vasculature relaxing agent provided by the covalent bond, the tissue-protective polypeptide (tpP) is further more effective by at least 5-50%, preferably 10-35%, as compared to the formulation without linking the tissue-protective polypeptide (tpP) and the triggering/vasculature relaxing agent together by a covalent bond.

Although formulations of the invention composed of the lipid, the polypeptide and the triggering agent, wherein the components are available as a mixture, are already very effective, the skin-protective effects can be further improved, if said components, preferably the polypeptides and the triggering agents according to the invention, are covalently linked together, or at least by ionic interaction.

The lipid compound or lipid structure in said cosmetic formulation or composition of the invention is associated to the tissue-protective polypeptide (tpP) by admixing or by ionic interaction or van der Waal forces. In a preferred embodiment the lipid compound thus forms a monolayer or a bilayer, such as a micelle or liposomal structure, in which the tissue-protective polypeptide is embedded or encapsulated.

The basis for the lipid environment of the tissue-protective peptides according to the invention can be provided, for example, by a phospholipid compound such as a, phosphatidylcholine, or a sphingolipid compound, such as a ceramide. However other lipid compounds or structures are suitable. The lipid components promote or enhance vessel relaxation, tissue regeneration/repair and transdermal penetration.

In some cases, it may be advantageous to link the lipid compound or lipid structure to the tissue-protective polypeptide by a covalent bond, thus providing a closer proximity to the respective target cells.

The triggering/vasculature relaxing agents according to the invention include amino acids, preferably in the L-form, such as L-arginine, L-phenylalanine, L-citrulline, and so on. It was found that polypeptides consisting of 2, 3 or 4 amino acid units of the same or of different amino acids may intensify the effects.

In a preferred embodiment, the triggering agent in this cosmetic formulation of the invention is selected from the group consisting of one or more amino acids or amino acid derivatives, selected from the group consisting of arginine, phenylalanine, lysine, glutamine, tyrosine, tryptophan, valine, proline, citrulline, creatine, taurine, and a polypeptide comprising or consisting of two or more identical or different amino acids as specified.

Specific amino acid entities comprising more than one unit are, for example:

- arginine, or a peptide consisting of 1-3 arginine molecules,
- citrulline, or a peptide consisting of 1-3 citrulline molecules,
- a peptide consisting of at least one L-arginine and one citrulline molecule,
- choline and/or vitamin B5, and/or vitamin E, and
- a compound consisting of choline and/or vitamin B5, and or vitamin E covalently linked to at least one arginine molecule and/or at least one L-citrulline,
- phenylalanine, lysine, glutamine, tyrosine, tryptophan, valine, creatine, or a polypeptide consisting of 1-3 of each of said amino acids, and
- a polypeptide comprising two or more different amino acids as specified.

In principal, all tissue-protective polypeptides according to the invention as specified above and below are suitable for use in the cosmetic formulations according to the invention.

In one embodiment, the tissue-protective polypeptide according to the invention consists of 7-40 amino acid residues. In particular, it consists of 7-30, or 11-15 amino acid residues. Preferred tissue-protective polypeptides of the invention comprise 7, 8, 9, 10, 11, 12, 13, 14, or 15 amino acid residues.

For example, the tissue-protective polypeptides in the formulations and compositions and in the conjugate molecules specified below according to the invention include the following known amino acid sequences:

5'-QQAVEVWQGLALLSEAVLRGQALLV-3' (SEQ ID NO: 3)
5'-RYLLEAKEAENITTGC-3'(SEQ ID NO: 5)
5'-APPRLICDSRVLERYLLEAKEAE-3' (SEQ ID NO: 7)
5'-FRKLFRVYSNFLRGKLKLYTGEACRTGDR-3' (SEQ ID NO: 9)
5'-MEVGQQAVEVWQGLALLSEAVLR-3' (SEQ ID NO: 11)
5'-TYSCHFGPLTWVCKPQGG-3' (SEQ ID NO: 13)
5'-KLKLYTGEACRTGDR-3' (SEQ ID NO: 15)
5'-WEHVNAIQEARRLL-3' (SEQ ID NO: 17)
5'-HADRELEKIGA-3' (SEQ ID NO: 19)
or a fragment thereof.

The polypeptides SEQ ID NOs: 3, 5 and 7 are fragments of the human EPO sequence (SEQ NO: 1). The other peptides derive from the interface of EPO and EPOR, the helix structure/face or comprise synthetic or different natural motifs, or share consensus sequences with fragments of Type I cytokine receptor ligands that have little or no potentially undesirable hematopoietic effects of the full length ligands. (e.g. WO 2009/094172).

It should be mentioned that the cosmetic formulations according to the invention principally work with the full EPO sequence as well. However the use of the disclosed polypeptides is more advantageous for different reasons.

In further embodiments, the cosmetic formulations, and conjugate molecules according to the invention include respective tissue-protective polypeptides which consist of not more than 40, preferably not more than 20, and not less than 7, in particular 7, 8, 9, 10, 11, 12, 13, 14 or 15 amino acid residues, are capable to bind to the erythropoietin receptor (EpoR) and/or the common ß receptor (ßcR), and preferably comprise a core sequences of the five amino acid residues LERAL.

In a preferred embodiment, the tissue-protective polypeptide (tpP) comprises or consists of variants of the 11-mer amino acid sequence QEQLERALNSS (SEQ ID NO: 21), wherein 1-4 amino acid residues, preferably 2, 3 or 4 amino acid residues of said amino acid sequence are replaced by conservative or non-conservative amino acid residue substitutions.

In particular, the invention provides isolated polypeptides which comprise the core sequence LERAL, derive from sequence SEQ ID NO: 2 by respective mutations, and comprise or consist of the generic amino acid sequence, presented by the sequence formula:

$X^1X^2X^3$ LERAL $X^4X^5X^6$ (SEQ ID 31)

wherein
$X^1$, $X^3$, $X^4$ are independently on each other Q or N
$X^2$ is E or D, and
$X^5$, $X^6$ are independently on each other S or T,
and wherein said polypeptide has skin-protective activity and does not or not essentially elicit hematopoietic or erythropoietic efficacy.

Variants having the core sequence LERAL and one amino acid substitution in each sequence triplet $(X^1X^2X^3)$ and $(X^4X^5X^6)$ left and right of the core sequence are preferred, because they elicit superior and further enhanced skin tissue protective efficacy.

In another preferred embodiment of the invention, the tissue-protective polypeptide (tpP) variant of this sequence (SEQ ID 31) comprises or consists of the 11-mer generic amino acid sequence, which has a core sequence of seven amino acids and is presented by the generic sequence formula:

$X^1X^2$QLERALN $X^5X^6$ (SEQ ID NO: 33), wherein $X^1$, $X^2$, $X^5$, $X^6$ have the meanings as specified above.

It was found that these polypeptide show superior efficacy in topical cosmetic skin treatment using cosmetic formulations according to the invention and are well compliant to the skin.

The polypeptide QEQLERALNSS (SEQ ID NO: 21, "Peptide 0"), falling under the generic sequence formula SEQ ID 31, is known e.g. from EP 2371855 as a compound which shows tissue-protective effects in parenterally applied therapeutic applications.

The following isolated polypeptides falling under the this generic sequence, were well investigated by the inventors of this application:

```
                                    (SEQ ID NO: 23)
        NEQLERALNTS ("Peptide 2")

(SEQ ID NO: 25)
        NEQLERALNST ("Peptide 1")

(SEQ ID NO: 27)
        QDQLERALNTS ("Peptide 4")

(SEQ ID NO: 29)
        QDQLERALNST ("Peptide 3").
```

Polypeptides comprising or consisting of these four amino acid sequences are most advantageous, and represent preferred embodiments of the invention. They show a distinctly higher efficacy in the cosmetic treatment of the skin, such as acne, wrinkles or skin ruptures and even anti-aging as compared to the reference known "Peptide 0".

In another preferred embodiment of the invention, the respective tissue-protective polypeptide (tpP) variant consist of the seven amino acids, presented by the 7-mer amino acid sequence: $X^3$ LERAL $X^4$ (SEQ ID 35), wherein $X^3$, $X^4$ have the meanings as specified above.

In another preferred embodiment of the invention, the respective tissue-protective polypeptide (tpP) variant consist of the nine amino acids, presented by the 7-mer amino acid sequence: $X^2X^3$ LERAL $X^4X^5$ (SEQ ID 37), wherein $X^2$, $X^3$, $X^4$, $X^5$ have the meanings as specified above.

Preferred cosmetic formulation of the invention comprise at least one of the polypeptide sequences as specified above, preferably together with at least one triggering/vasculature relaxing agent and/or a lipid compound or lipid structure.

Alternatively to formulations or compositions, the invention provides conjugate molecules suitable for cosmetic use.

Thus, in one aspect of the invention, a conjugate molecule is provided, formed at least between a tissue-protective polypeptide (tpP) and a triggering/vasculature relaxing agent by covalent bonding.

In a second aspect, a conjugate molecule is provided, formed at least between a tissue-protective polypeptide (tpP) and a lipid compound or lipid structure by covalent bonding. And finally, a conjugate molecule is provided, formed at least between a tissue-protective polypeptide (tpP), a triggering/vasculature relaxing agent, and a lipid compound or lipid structure by covalent bonding, wherein in each of these alternatives the components of the conjugate molecule are applied as specified above, below and in the claims.

As already mentioned above, the lipid environment, like a micelle or liposome, or another monolayer or bilayer structure in the cosmetic formulations comprising such conjugate molecule, is enabled to promote penetration of said tissue-protective polypeptide, and optionally a second cell-active agent linked thereto, to the skin cells, preferably to the competent target-oriented cells, preferably CD90+ cells of skin tissue. The lipid components of the conjugate molecule promote or enhance vessel relaxation, tissue regeneration/repair and transdermal transport and penetration as well.

In another aspect, the conjugate molecule is formed at least between a tissue-protective polypeptide (tpP) and triggering/a vasculature relaxing agent by covalent bonds, wherein the tissue-protective polypeptide (tpP) is one of the polypeptides represented by the amino sequences shown above and in the claims, and wherein the triggering agent shall stimulate directly or indirectly nitric oxide and/or acetylcholine production in said cells. In this conjugate molecule, said tissue protective polypeptide is linked to said triggering/vasculature relaxing agent, preferably by covalent bonding.

In a preferred embodiment of the invention, this conjugate molecule between covalently linked tissue-protective polypeptide (tpP) as specified and triggering agent as specified, is associated or linked by ionic interaction or van der Waal forces to a lipid compound, such phosphatidylcholine or ceramide, or is embedded within a micelle or liposome structure.

In a preferred embodiment, the triggering/vasculature relaxing agent in this conjugate molecule of the invention is selected from the group consisting of:

L-arginine, or a peptide consisting of 1-3 L-arginine molecules,

L-citrulline, or a peptide consisting of 1-3 L-citrulline molecules, a peptide consisting of at least one L-arginine and one L-citrulline molecule, choline and/or vitamin B5, and a compound consisting of choline and/or vitamin B5 covalently linked to at least one L-arginine molecule and/or at least one L-citrulline molecule.

phenylalanine, lysine, glutamine, tyrosine, tryptophan, valine, creatine, or a polypeptide consisting of 1-3 of each of said amino acids, and a polypeptide comprising two or more different amino acids as specified.

The conjugate molecules according to the invention can be represented by the following structures:

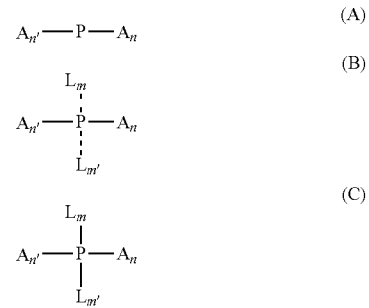

wherein

| | |
|---|---|
| P | represents a tissue-protective polypeptide (tpP), preferably a polypeptide of any of the the amino acid sequences as specified herein |
| A | represents one or more identical or different triggering agents; preferably A represents L-arginine, L-citrulline, choline, vitamin |
| L | represent one or more identical or different lipid components or structures |
| - | represents a covalent bond |
| I | represents a ionic interaction or caused by van der Waal forces |
| n, n' | represents an integer 0, 1, 2, 3, 4, 5-10 |
| m, m' | represents the integer 0 and 1 wherein at least n or n' or m or m' = 1. |

Preferred embodiments of the conjugate molecules according to the invention can be selected from the following group:

P—arginine
P—arginine-arginine
P—arginine-arginine-arginine
arginine—P—arginine
arginine-arginine—P—arginine-arginine
P—choline
P—arginine—choline—vitamin B5
P—choline—vitamin B5
P—arginine-arginine—choline
P—arginine-arginine—choline—vitamin B5
P—citrulline
P—citrulline—citrulline
P—arginine-arginine—citrulline
P—arginine-arginine—citrulline—citrulline
arginine-arginine—P—arginine-arginine—choline
arginine-arginine—P—arginine-arginine—choline—vitamin B5
citrulline—arginine—P—arginine—citrulline, citrulline—citrulline—arginine—arginine—P—arginine—arginlne—citrulline—citrulline, citrulline—citrulline—arginine—arginine—P—arginine—arginine—citrulline—citrulline—vitamin B5, wherein P represents the respective tissue-protective polypeptide as specified herein, and "—" represents a covalent bond, Especially P means one of the polypeptides presented by the amino acid sequences:

QEQLERALNSS ("Peptide 0") (SEQ ID NO: 21)

NEQLERALNST ("Peptide 1") (SEQ ID NO: 25)

NEQLERALNTS ("Peptide 2") (SEQ ID NO: 23)

QDQLERALNST ("Peptide 3") (SEQ ID NO: 29)

QDQLERALNTS ("Peptide 4") (SEQ ID NO: 27)

As already outlined above, the tissue-protective polypeptides (tpP) as specified above and in the claims including the specific amino acid sequences, are linked to the triggering agent as specified above and in the claims, to form the conjugate molecules of the invention.

Preferred conjugate molecules according to the invention are

QEQLERALNSS-R (SEQ ID NO: 21)

NEQLERALNTS-R (SEQ ID NO: 23)

NEQLERALNST-R (SEQ ID NO: 25)

QDQLERALNTS-R (SEQ ID NO: 27)

QDQLERALNST-R (SEQ ID NO: 29)

R-QEQLERALNSS-R (SEQ ID NO: 21)

R-NEQLERALNTS-R (SEQ ID NO: 23)

R-NEQLERALNST-R (SEQ ID NO: 25)

R-QDQLERALNTS-R (SEQ ID NO: 27)

R-QDQLERALNST-R (SEQ ID NO: 29)

R-QEQLERALNSS (SEQ ID NO: 21)

R-NEQLERALNTS (SEQ ID NO: 23)

R-NEQLERALNST (SEQ ID NO: 25)

R-QDQLERALNTS (SEQ ID NO: 27)

R-QDQLERALNST, (SEQ ID NO: 29)

wherein R is the triggering/vasculature relaxing agent and is preferably selected from the group consisting of (L-arginine)$_n$, (L-citrulline)$_m$, choline and vitamin B5, wherein n, m are independently of each other 1, 2 and 3.

The outcome of the invention can be summarized as:

The tissue-protective polypeptides, conjugate molecules and formulations as specified herein do penetrate actively, in an assisted manner or passively through the superficial skin layers.

There is a controlled target capacity or residence preference in one or more areas of the skin and a controlled targeting to specific cells of the skin is achieved.

The tissue-protective polypeptides, conjugate molecules and formulations have a significantly reduced percentage of proteolytic degradation, and are well tolerated by the skin.

The tissue-protective polypeptides, conjugate molecules and formulations can exert their function at the targets in the skin.

The cosmetic effects against aging of the skin or acne or skin irritation by UV irradiation are visible.

The risk of cancer initiation is converted to the opposite using the tissue-protective polypeptides, conjugate molecules and formulations of the invention, which are protective molecules.

Complex interacting triggering entities are generated which achieve tissue repair and tissue regeneration contradictory to current teaching and are based upon multi-causal interaction and abilities to interact.

The lipid composition according to the invention preferably, based on ceramides and/or phosphatidylcholines or similar sphingolipids or phospholipids, supports significantly skin repair, skin regeneration and skin rejuvenation of the polypeptides alone and, above all, in combination with the triggering/vasculature relaxing agents as specified, compared to a standard cosmetic lipid formulation.

The newly synthesized polypeptides of the invention ("Peptides 1-4") show at least regarding some physiological and physical properties enhanced efficacy compared to the known polypeptide ("Peptide 0"), represented by SEQ ID NO: 21.

DETAILED DESCRIPTION OF THE INVENTION

Figure 1:
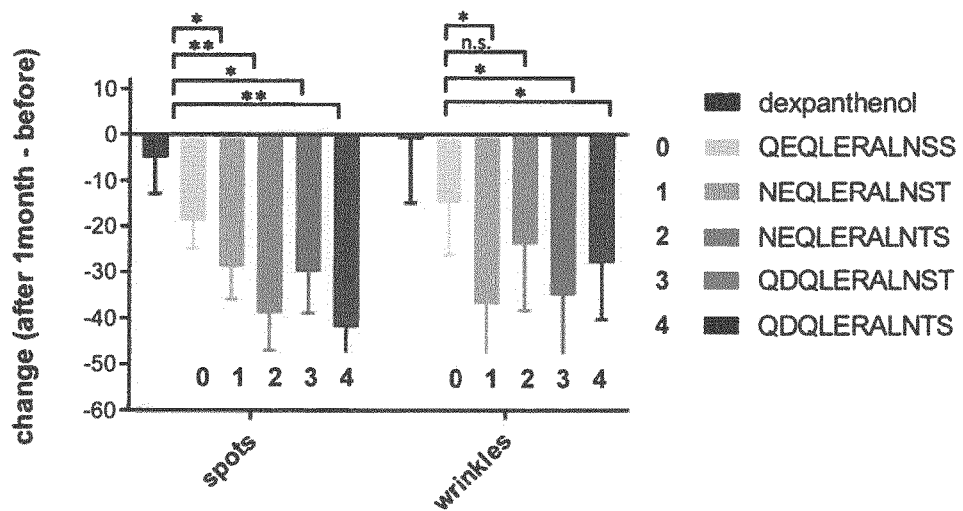
FIG. 1 shows the efficacy of the tested polypeptides (Peptides 0, 1, 2, 3 and 4) and spots and wrinkles parameter changes after 1 month of formulation application.

The term "peptide conjugate" as used in this application means any kind of linkage between the tissue-protective peptide an a lipid compound and/or a triggering agent. As a rule the linkage is covalent bond, preferably between the peptide and the triggering agent. However, also the lipid compound may be coupled to the peptides according to the invention via a covalent bond. The term peptide-conjugate used in this application comprises also bonds between the two entities based on stronger ionic or van der Waal interactions. The latter one favour the (self)generation of monolayer and bilayers of lipid structures, such as micelles and liposomes. The term expressively includes a functionally effective construct formed by a peptide and another functionally different molecule, e.g. a lipid compound and/or a triggering agent linked to each other by van der Waals bonding (ionic interaction). In general any functionally active group (like —OH, —NH2) within the peptide structure can be used for linking by covalent bonds with a functionally active group of the lipid compound or the triggering/vasculature relaxing agent according to methods well known in the art. Preferably, the respective groups at the N-terminus and/or the C-terminus of the peptide or in the near vicinity thereof are used for binding.

The term "tissue-protective peptide" as used herein, means a peptide that elicits to the targeted tissue a protective effect against cell damage, and cell aging caused by inner and outer influences. The protective effect appears when tissue defects are prevented or the original intact status of the cell is restored.

The terms "triggering agent" or "triggering/vasculature relaxing agent" mean an agent that stimulates vasculature relaxation and/or supports transport of the tissue-protective polypeptide (tpP) to the CD90 expressing skin cells, and includes according to the invention selected amino acids, preferably in their L-form, and specific vitamins.

The term "EPO variant/analog/fragment/mimetic, as used herein, means a peptide having a shorter and/or different an amino acid sequence compared to native human erythropoietin, and binds to or interact with the EPO receptor (EpoR) and the common ß receptor (cBR), these receptors forming a heteroreceptor. Such peptide elicits a tissue protective or tissue regenerative efficacy and no or no significant hematopoietic effect.

The term "hematopoietic activity/efficacy" means any significant increase in blood cellular components such as erythroid, lymphoid, and myeloid cells. Further hematopoietic activity refers to whether an isolated peptide or peptide analog possess activity selected from vasoactive action (e.g., vasoconstriction), hyperactivating platelets, pro-coagulant activities, and stimulating proliferation or production of thrombocytes or erythropoietin-dependent cells.

Phosphatidylcholines (PC), as used herein, are a class of phospholipids that incorporate choline as a headgroup. In more detail, it is composed of a choline head group and glycerophosphoric acid, with a variety of fatty acids. Usually, one is a saturated fatty acid (e.g. palmitic or hexadecanoic acid, $HsC-(CH_2)_{14}-COOH$; or heptadecanoic acid $H_3C-(CH_2)_{15}-COOH$); and the other is an unsaturated fatty acid (e.g. oleic add, or 9Z-octadecenoic acid, as in lecithin). PC are a major component of biological membranes and can be easily obtained from a variety of readily available sources, such as egg yolk or soybeans. Although phosphatidylcholine has been used as an ingested supplement, it is also included as an ingredient in topical skin creams, and can create smoother skin, increase skin's moisture level, condition skin and hair, support skin regeneration, and supply both choline and linoleic acid.

Ceramides, as used herein, belong to the general class of sphingolipids and are a major component of the skin and especially in the upper layers of the epidermis in the stratum corneum. A number of types of ceramides exist, depending on their location and their function in the epidermis. The term ceramide comprises solely lipids composed of the sphingosine family, such as sphinganine, 4-hydroxy-sphinganine or phyto-sphingosine, which are bonded to a fatty acid or fatty acid derivative via their amine functional group. The lipids of the intercorneocytic cement of the skin, and in particular the ceramides, are arranged in lamellar double layers, or lamellae, and take part in the cohesion of the stratum corneum for the purpose of keeping the barrier whole and for maintaining its protective, anti-penetration or anti-irritant role, and the like.

Liposomes, as used herein, are composed of a lipid bilayer separating an aqueous internal compartment from the bulk aqueous phase. Micelles as used herein, are closed lipid monolayers with a fatty acid core and polar surface, or polar core with fatty acids on the surface (inverted micelle).

Controlled penetration through intact skin and persistence within the skin is surprisingly found when linking the EPO peptides of the invention to phosphatidylcholins and ceramides. These are lipid structures which, if linked to erythropoietin or EPO peptides according to the invention through ionic (van der Waal) interactions and micelle formation, enhance the lipid layer persistence of the EPO analogs in the skin. These combinations create a lipid structure and localized resorption within the skin layer but do not allow resorption into deeper areas. The combined presence of phosphatidylcholines, lecithins and ceramides adds this lipophilic physicochemical property to erythropoietin and its peptide analogous that allow a mode of action to occur that would otherwise be absent due to lack of accessibility of the intact skin layers of the protein erythropoietin into the intact skin while at the same time targeting the skin area rather than allowing a unspecific gradient based distribution.

The compositions of the invention contain lipid ingredients forming lamellar structures, and include phosphatidylcholines, lecithins, ceramides and triglycerides which are non-toxic even in concentrations of up to 40%-50% or more. Ceramides and/or phosphatidylcholines are the preferred components (5-70%) of the lipid composition according to the invention.

The polypeptide conjugates of the invention provide controlled target capacity or residence preference in one or more areas of the skin and controlled targeting to specific cells of the skin. Also a persistence in these layers and binding to cell membranes is possible.

This allows to reduce the amount of EPO derived peptides used normally from 100-400 Units kg/body weight to 5-12 Units per kg body weight or even less to 1 Unit/kg body weight and targets a specific skin area of approximately 100 $cm^2$.

The therapeutic range is even going down to 0.1-0.5 Units per kg of body weight but can be safely extended to 40 units of kg bodyweight. The ideal range is thus 0.1% percent and less of a conventional form of application. This contributes significantly to drug safety and reduction of side effects of EPO and its analogues.

The term "peptide conjugate/conjugate molecule" as used in this application means any kind of linkage between the tissue-protective peptide an a lipid compound and/or a triggering agent. As a rule the linkage is covalent bond, preferably between the peptide and the triggering agent. However, also the lipid compound may be coupled to the peptides according to the invention via a covalent bond. The term peptide-conjugate used in this application comprises also bonds between the two entities based on stronger ionic or van der Waal interactions. The latter one favour the (self)generation of monolayer and bilayers of lipid structures, such as micelles and liposomes. The term expressively includes a functionally effective construct formed by a peptide and another functionally different molecule, e.g. a lipid compound and/or a triggering agent linked to each other by van der Waals bonding (ionic interaction). In general any functionally active group (like —OH, —NH2) within the peptide structure can be used for linking by covalent bonds with a functionally active group of the lipid compound or the triggering agent according to methods well known in the art. Preferably, the respective groups at the N-terminus and/or the C-terminus of the peptide or in the near vicinity thereof are used for binding.

The term "tissue-protective peptide" as used herein, means a peptide that elicits to the targeted tissue a protective effect against cell damage, and cell aging caused by inner and outer influences. The protective effect appears when tissue defects are prevented or the original intact status of the cell is restored.

The term "EPO variant/analog/fragment/mimetic, as used herein, means a peptide having a shorter and/or different an amino acid sequence compared to native human erythropoietin, and binds to or interact with the EPO receptor (EpoR) and the common ß receptor (cßR), these receptors forming a heteroreceptor. Such peptide elicits a tissue protective or tissue regenerative efficacy and no or no significant hematopoietic effect.

Also to achieve the tissue specific effects of EPO and thus its desired tissue regenerative activity as a tissue protective and regenerative molecule is not only linked according to the invention to the ability to reach the target area but also on so called "bystanders" being a single or complex mixture of adjuvants or co-signals being chemically or structurally independent or at least different from EPO and its analogs.

It is this lack of mono-causality that has led to failures or limited functionality in intact and or even opened skin (wound) applications of the use of EPO as a single molecule alone. It is the purpose of this invention to overcome these limitations by creating a new formulation of erythropoietin and/or its analogues as a tandem, triple, quadruple and further multiples of this ratio in a linkage condition to different molecules (single individuals or multiples of it). These molecules can be linked either chemically in a reversible or non-reversible or used in a micelle way or encapsulating form or EPO being bound reversibly or non-reversibly to a carrier molecule, nano- or microstructure.

There are multiple advantages of creating not only resistance to degradation, a controllable dynamic availability in intact skin or specific targeted tissues and to unleash unknown activities or activities not possible conventionally while at the same time increasing specificity and safety of use. This methodology (method of use) or new complex chemical entities are not only applicable to the skin but also to deeper and heterogenous internal targets inside the human or animal body, depending upon the specialisation and strategy selected.

Vitamins in combination with erythropoietin structures including the tissue-protective peptide conjugates of the invention undergo ionic bindings and are relevant to trigger cascade activities. The tissue protective properties of EPO or its analogues cannot be effective if a directed targeting to tissue repair is not possible. Especially in aged skin or even in open wounds EPO alone cannot show activities.

Thus the combination of the peptide conjugates according to this invention with vitamin A supports neurogenic regeneration, with vitamin B 1-6 trophic regenerations, with vitamin C neuronal sprouting and wound closure, and with vitamin B12 anti-inflammatory activities.

All these activities elicit yes-or-no answers. This means the presence of these molecules in a combination turn the trigger to yes, one of the factors alone by itself cannot achieve this effect, this leaves the cellular target at a "no" answer.

Thus it is favourable according to this invention to combine the tissue-protective peptides as specified above and in the claims with vitamins such as vitamin A, B1-6, B12, and C in order to enhance the skin protective effect in topical cosmetic applications.

Favorable applications include enhancement of glowing skin and acceleration of skin repair by a relaxation of the vessels. This can be achieved by various agents that trigger the availability of nitric oxide in the respective skin cells.

Nitric oxide is biosynthesized endogenously from L-arginine, oxygen, and NADPH by various nitric oxide synthase (NOS) enzymes. The endothelium of blood vessels uses nitric oxide to signal the surrounding smooth muscle to relax, thus resulting in vasodilation and increasing blood flow. Conversely, L-arginine is metabolize to release nitric oxid. Nitric oxide (NO) continues to stimulate guanylyl cyclase to make cGMP. cGMP induces relaxation of the muscle cells in the vasculature walls. This is also the location of the CD90+ cells that are targeted by the remaining peptide structure.

It is the phosphatidylcholine and ceramide complex that allows the structure to penetrate the skin and reach the vasculature area of the skin.

To this purpose L-arginine may be linked to the tissue-specific peptides of the invention and/or mixed with the phosphatidylcholines and/or ceramides in a micellar or liposomal structure in order to obtain the peptide conjugates as disclosed in this patent application. It is also favorable to add free L-arginine and other amino acids in the cosmetic formulation of the invention in addition to said peptide conjugates.

It could be surprisingly found that arginine as well as other amino acids, such as L-phenylalanine, L-lysine, L-tryptophan, L-proline, L-glutamine mixed with said lipid compounds, preferably ceramides, and phosphatidylcholines (lecithins) effect a close vicinity to the microenvironment of the specific skin cells, here CD90 positive skin cells and render them sensitive for targeting molecules such as the tissue-protective polypeptides according to the invention. Interestingly, the lipid formulation aooording to the invention solely without a CD90 cell targeting peptide is already tissue protective versus a standard lipid formulation which is used for skin cosmetic (5-15% improvement versus a standard lipid composition under the same conditions dependent on the standard lipid composition used). However, in combination with a tissue-protective polypeptide according to the invention, this effect is further enhanced until 10% versus the lipid composition of the invention without said tissue-protective peptides, and until 25% compared to a standard lipid composition without a respective tissue-protective polypeptide usually offered in cosmetic treatments. The effects of these formulation mixtures are comparable to those which can be achieved with conjugate molecules according to the invention, wherein the tissue-protective polypeptide is linked by covalent bonding to the triggering agent, such as a respective amino acid molecule, like L-arginine. Therefore conjugate molecules according to the invention provide only advantages versus a mixture of the two respective components of the conjugate molecule, if they are formulated with a lipid composition used in standard cosmetic products, whereas the use of the conjugate molecules are often superfluous and can be replaced by a mixture of the components of the conjugate molecules when a lipid compound/composition as disclosed by this invention is used.

In this area vessels antagonized effect to locally present phospodiesterases by providing more locally available cGMP. This favorable microenvironment is inducible for better nourishing the skin. The dual effect of the invention is however a dramatic increase of local CD90+ tissue repair activity since complementary microenvironmental factors can reach the local area better due to improved vasculature nutrient and oxygen supply as well as waste removal.

As already mentioned, the effect of EPO and EPO analogs, such as the respective peptides and peptide conjugates of the invention, on skin tissue targeting, is significantly enhanced if bound to or embedded in lipid structures such as the phosphatidylcholines or ceramides. A similar effect can be observed, if sugar molecules, like glucose and the like is provided in the Formulation according to the invention.

By this, the molecule is placed like a back pack on the molecule and then transported preferentially inside the body across (sugars) or into the skin. This allows to use smaller quantities and target energy consuming tissues like brain or muscles as well as zones of inflammation. The sugar entities transport the EPO and its analogues to the tissues with high metabolic activities such as the brain or muscles.

L-Arginine is one of the most metabolically versatile amino acids. In addition to its role in the synthesis of nitric oxide, L-arginine serves as a precursor for the synthesis of polyamines, proline, glutamate, creatine, agmatine and urea. Several human and experimental animal studies have indicated that exogenous l-arginine intake has multiple beneficial pharmacological effects when taken in doses larger than normal dietary consumption. Such effects include reduction in the risk of vascular and heart diseases, reduction in erectile dysfunction, improvement in immune response and inhibition of gastric hyperacidity.

However, current interest in l-arginine is focused mainly on its close relationship with the important signal molecule nitric oxide (NO). l-Arginine is the only substrate in the biosynthesis of NO, which plays critical roles in diverse physiological processes in the human body including neurotransmission, vasorelaxation, cytotoxicity and immunity. Arginine, preferably L-arginine, is added according to the invention to the peptides in front and at the end and also as multitude of 1 up to e.g. 10, or more molecules arginine preferably 1-3.

Choline is used for synthesis of acetylcholine. This molecule besides NO is involved in smooth muscle cell relaxation. Thus targeting the CD90+ cell in the vasculature wall enhances the combined effect of arginine. Vitamin B5 is necessary for the metabolism of choline in order to make the acetylcholine neurotransmitter. Therefore, the effect of choline can be enhanced by combing t with vitamin B5. Yohmibin ($C_{21}H_{26}N_2O_3$) is a natural compound which blocks alpha 2 adrenergic receptors in smooth vessel cells thus leading to vasculature relaxation. Yomibin can be added to the phosphatidylcholines, ceramides or lipid parts of the structures according to the invention.

The polypeptide conjugate molecules and the isolated polypeptides as disclosed herein according to the invention can be used in a topical formulation applied to the skin preferably in the range of 0.001 to 9.999 µg of EPO derived tissue-protective peptide per $cm^2$, more preferably in the range of 20 to 50 units per $cm^2$, but ideally not more than 100 Units per $cm^2$. At higher concentration micro-angiogenesis is induced as a relevant side effect.

Synthesis of the Polypeptides According to the Invention:

Tissue protective polypeptides of the current invention can be produced using standard techniques including those involving chemical synthesis and those involving purification from a cell producing the polypeptide. Techniques for chemical synthesis of polypeptides are well known in the art. (See e.g., Vincent, Peptide and Protein Drug Delivery, New York, N.Y., Decker, 1990.) Techniques for polypeptide purification from a cell are ilustrated in the Examples provided below. Additional examples of purification techniques are well known in the art. (See for example, Ausubel, Current Protocols in Molecular Biology, John Wiley, 1987-2002). Obtaining polypeptides from a cell is facilitated using recombinant nucleic acid techniques to produce the polypeptide. Recombinant nucleic acid techniques for producing a polypeptide involve introducing, or producing, a recombinant gene encoding the polypeptide in a cell and expressing the polypeptide. A recombinant gene contains nucleic acid encoding a polypeptide along with regulatory elements for polypeptide expression. The recombinant gene can be present in a cellular genome or can be part of an expression vector. Expression of a recombinant gene in a cell is facilitated through the use of an expression vector. Preferably, an expression vector in addition to a recombinant gene also contains an orig in of replication for autonomous replication in a host cell, a selectable marker, a limited number of useful restriction enzyme sites, and a potential for high copy number.

Tolerance Assay of Some Tissue Protective Polypeptides of the Invention

Patch test was performed on 30 subjects in calendar week 35. Then 22 from 30 treated subjects have been repeated this patch test at same areas in calendar week 39. Additional to 22 subjects that were repeatedly treated with the same lipid composition according to the invention comprising Peptides 0-4 additional subjects (new) joined to this trial. The objective of the study was to detect secondary skin irritation allergic sensitization to the test substances 2, 3 and 4 weeks after first treatment. The test substances were applied with the same concentration of the peptides applied to the skin. The patch limits contact of the panelist's skin with the test substance to a local area and exposure is exaggerated due to the occlusive conditions. The skin was checked at 24, 48 and 72 hours.

CONCLUSION: No evidence of any skin disorder was detected in the test area of any of the 30 panelists after conducting patch testing for 24 h, 48 h and 72 hours according to the internationally recognized guidelines of ICDRG (International Contact Dermatitis Research Group). Also, among 22 subjects that received secondary irritation. It can be concluded that the use of the product will not cause any unwanted skin reactions due to a secondary (repeatedly) irritating effect.

Polypeptides Used in Cosmetic Trials According to the Invention:

Synthetic Peptides:

```
                              (SEQ ID NO: 23)
    NEQLERALNTS ("Peptide 2")

(SEQ ID NO: 25)
    NEQLERALNST ("Peptide 1")

(SEQ ID NO: 27)
    QDQLERALNTS ("Peptide 4")

(SEQ ID NO: 29)
    QDQLERALNST ("Peptide 3")

(SEQ ID NO: 21)
    QEQLERALNSS ("Peptide 0")
```

EPO-Fragments:

```
                                  (SEQ ID NO: 3)
    QQAVEVWQGLALLSEAVLRGQALLV     (Fragment 1)

(SEQ ID NO: 5)
    RYLLEAKEAENITTGC              (Fragment 2)

(SEQ ID NO: 7)
    APPRLICDSRVLERYLLEAKEAE       (Fragment 3)
``` and full length EPO.

Cosmetic Application Trials (General):

In a blinded observation 45% of 20 users cases improved wrinkle reduction (56%), increased blood flow as evidenced in the area by thermographic heat measurement (35% increase), and had thus a lasting improvement for vasculature rejuvenation. The area of applications is a skin balm to increase the glow, a cosmetic formulation for the skin to increase the glow of the lips. In another application in male health area, for erectile dysfunction the cream is topically applied to the skin of the penis and to target vasculature repair and vasculature inflow.

To strengthen such effects significant amounts of arginine (10-100 mg/g formulation) was added. The advantage of this combined approach is the CD90+ medicated repair and the vasculature supply effect for skin beauty, rejuvenation but also in higher concentration for repairing vasculature deficits in erectile dysfunctions.

It is also possible according to this invention to combine the peptide conjugates with naturally derived compounds which increase naturally nitric oxide formation and availability in the skin in order to improve efficacy. Cosmetic formulations according to the invention can be enriched with such compounds preferably derived from vitamins, such as vitamin C, D, E, A and B12, and natural food resources, like, for example, spinach, beets, celery, garlic, aragula lettuce, iceberg lettuce, carrots, parsley, cabbage, radishes, collard greens, grape seed extracts, natural substance which blocks the conversion of testosterone to estrogen, group of procyanidins. Thus, the nitric endothelial output can be increased by 200%, and natural glow, skin rejuvenation and repair was significantly (45% over controls) enhanced.

To the cosmetic formulation further adjuvants and additives can be added to broaden or enhance the described effects of the tissue-protective peptides and peptide conjugates according to the invention. Such agents are, for example:

Pycnogenol or Q10 (coenyme)

*Ginseng* extracts,

Quercetin extracts, it is a flavonoid, resveratrol, procyanidin, tannins, tea catechins, genistein increase nitric oxide levels in the skin. Piperin enhances resveratrol (black pepper extract). Skin food quercetin extracts are obtained eg. from Onions, garlic, chives, apples, grapes, and red wine as a natural source, nuts and and spinach. Salmon, grassfed red meat, animal organs, egg yolks are alternative sources to synthesis.

Niacin increases nitric oxide synthase, and thus, baseline NO levels

Alkaloid extracts from the cayenne pepper (or other hot chills)

Caffeine free coffee extract rich in antioxidants to increase nitric oxide.

Raw cacao actually contains the same nitric oxide boosting active compound as pycnogenol and grape seed extract do (protocyanidin), along with many other NO boosting antioxidants.

Icariin is a flavonoid of herbal (epimedium, horny goat weed). The herb is added topically to allow according to the invention a direct in impact on the skin a testosterone enhancing activity. Icariin supports nitric oxide production and is a moderate inhibitor of phosphodiesterase 5 (PDE-5).

Omega-3' and Omega-6' fatty acids if added to the lotion support a anti-inflammatory function, increase blood flow and nitric oxide levels.

Peptide Delivery Formulation

The formulations of this innovation can be combined with any cream or lotion. For that purpose, the conventional cream or lotion (final 99% mass/mass) is mixed with compositions comprising a tissue-protective polypeptide of the invention, one or more triggering/relaxing agents as specified and a lipid compound or structure based on sphingolipids or phospholipids described herein (0.5-3%, e.g. 1% w/w), referred to as 'trigger factor complex'. Due to the small fraction in the final mixture, the trigger factor complex does not change the overall physical properties of the cream or lotion, e.g. emulsion stability or moisturizing properties.

The trigger factor complex contains the following ingredients in decreasing concentration: water, ethanol, glycerol, vitamin E acetate, hydrogenated lecithin, cholesterol, L-arginine, L-phenylalanine, L-lysine, L-alanine-glutamine, L-tryptophane, L-tyrosine, L-valine, L-Prolin, L-taurine, ceramide NG, ceramide NP, oleic acid, palmitic acid, sodium ascorbate, phenoxyethanol, mustard seed oil, EDTA, oligopeptide.

For example, the trigger complex is composed of (Table 1)

| INGREDIENT | FRACTION (MASS/MASS) OR CONCENTRATION |
| --- | --- |
| Cerasome 9041/lipid base with ceramide (or phosphatidylcholine | 30-75%, e.g. 54%-55% |
| Vitamin E acetate | 10% |
| PEPHA ® AGE | 15% |
| Taurin/Arg/Ala-Gln, Lys, PheAla, Try, Tyr, Val, Pro water solution | combined: 10% (all at equal concentrations) |
| Mustard seed oil | 0.01% |
| Glycerine | 10% |
| Tissue-protective peptide of the invention, such as Peptides 0, 1, 2, 3, 4 | 50-500 ng/ml preferably 50-200 ng/ml, e.g. 95 ng/ml |

This invention includes peptide delivery formulations based on lotions (low lipid content) and formulations based on creams (high lipid content). Creams are typically optimal for dry skin, because the help keeping the skin moist. Lotions are less greasy, more easily absorbed into the skin and are optimal for normal skin. However, both lotion and cream in combination with tissue-protective and triggering/vasculature relaxing agents presented in this invention are optimized for optimal overall skin improvement. As a result, a tissue-protective peptide delivering formulation is not limited to either cream or lotion but can be chosen according to the skin type.

Nds Cream:

The NDS cream consists of the cream base (99% mass/mass) and the trigger factor complex (1% mass/mass).

Cream Base:

The cream base contains water, *Helianthus annuus* seed oil, pentylene glycol, squalene, octyldodecanol, argania *spinosa* kernel oil, ethylhexyl stearate, *persea gratissima* (avocado) oil, tribehenin, polyglycerol-3 polyricinoleate, sorbitan oleate, shea butter, sorbitol, *Oenothera biennis* (evening primrose) oil, and tocopheryl acetate.

iARP Lotion:

The iARP lotion consists of the lotion base (99% mass/mass) and the trigger factor complex (1% mass/mass).

Lotion Base:

The lotion base contains water, caprylic/capric triglyceride, pentylene glycol, propylene glycol, hydrogenated phosphatidylcholine and glycerine.

Cerasome 9041:

Cerasome 9041 was purchased from lipoid GmbH and contains ingredients according to the following table (Table 2)

| ingredient | fraction (mass/mass) |
| --- | --- |
| water | >50% |
| ethanol | 10-25% |
| hydrated lecithin | 1-5% |
| cholesterin | 1-5% |
| ceramid II | 0.1-1% |
| ceramid III | 0.1-1% |
| oleic acid | 0.1-1% |
| palmitic acid | 0.1-1% |
| sodium ascorbate | <0.1% |
| EDTA | <0.1% |
| sodium hydroxide | <0.1% |

Pepha® AGE:

Pepha AGE is a *Scenedesmus rubescens* (freshwater green algae) extract and was purchased from DSM Nutritional Products GmbH. This extract is claimed to enhance production of Collagen III and attenuate sunbumrn-induced skin damage. The extract contains amino acids, vitamin B3, algal saccharides and zinc.

Efficacy Tests

To assess the efficacy of the formulations of this invention in a human skin context an erythema recovery assay and a cosmetic skin improvement assay were performed.

Cosmetic Skin Improvement Assay:

In this assay the cosmetic facial skin appearance upon application of the formulations of this invention was monitored. For that purpose, the commercially available state-of-the-art facial skin imaging and data analysis platform, the Canfield Bio Visia™, was utilized, (see here: https://www.canfieldsci.com/imaging-systems/visia-complexion-analysis/). This platform provides the possibility of a i) highly standardized, ii) highly reproducible, iii) quantitative, iv) non-invasive, and vi) subject or tester bias-free skin quality analysis. It records several photos of the face from different angles and records absorption/reflection spectra (see figure: Canfield VISIA facial skin analysis platform). Using these data, the platform quantifies several parameters of skin quality, including 'spots', 'wrinkles', 'pores', 'smoothness', 'UV spots', and 'brown spots' (see figures: skin parameters 1-3). The in-built software standardizes every parameter by comparison to a large database of skin feature norms and returns a value in the range of 0%- to 100% to permit inter-individual subject comparison.

Healthy subjects received cosmetic creams with formulations of this invention or controls in a blinded manner, i.e. the subjects were unaware of the identity of the received cosmetic cream. Subjects were instructed to apply the cream once a day in the evening and on how much to apply. Subject skin quality was assessed before the start of the application and after one month (31±3 days). As a control, to account for seasonal and lifestyle change associated skin quality changes, quality of the hand exterior surface was monitored as well. The hypothetical option of using left and right side of the face for cosmetic treatment and internal control was not used to exclude subject compliance as a major confounder. For instance, non-complying subjects could decide to just apply the cream to both halves of the face, erroneously swap application and control half or decide to apply another cosmetic product to the control side. Application-induced noticeable improvements in skin quality on the application but not control side could have manifested in a bizarre overall face appearance, thereby presenting a strong incentive for subjects not to comply with such assay instructions. Nevertheless, exterior hand surface skin quality did not change statistically significantly in any subject, thereby indicating that the assay duration did not correlate with any lifestyle or seasonal change in overall skin quality.

By contrast, application of the formulations of this invention statistically significantly improved the skin quality compared to the controls. Since the data are paired (before application, after one month) for each subject and parameter, the difference (parameter value after 1 month–parameter value before application) permits intra-subject normalization and enables good inter-subject comparability. Dexpanthenol, a provitamin of vitamin $B_5$, is commonly used in both cosmetic skin care creams and medical skin treatments and also exerts a tissue-protective effect in skin. Thus it was chosen as a control reference. However, the advanced peptide-delivery formulations of this inventions performed better in improving the measured skin parameters, such as spots, wrinkles and smoothness (see figure). Moreover, the formulations with the tissue-protecive peptides of this invention (NEQLERALNST, NEQLERALNTS, QDQLERALNST or QDQLERALNTS) performed even better than the formulations with the previously described QEQLERALNSS peptide. For instance, formulations with any of the four novel tissue-protective peptides of this invention statistically significantly reduced spots to a greater extent than the formulation with the QEQLERALNSS peptide.

FIG. 1: shows the efficacy of the tested polypeptides (Peptides 0, 1, 2, 3 and 4).

Spots and wrinkles parameter changes after 1 month of formulation application.

Reduction of spots and wrinkles is a cosmetic benefit. Bars represent mean change and standard deviation of the mean change. Statistical analysis was performed in Graph-Pad Prism 7 using a one-way ANOVA. Significance levels are 0.05 (*) and 0.01 (**). Dexpanthenol (final 5% mass/mass) and the peptides were delivered by a cream.

Figure 2:
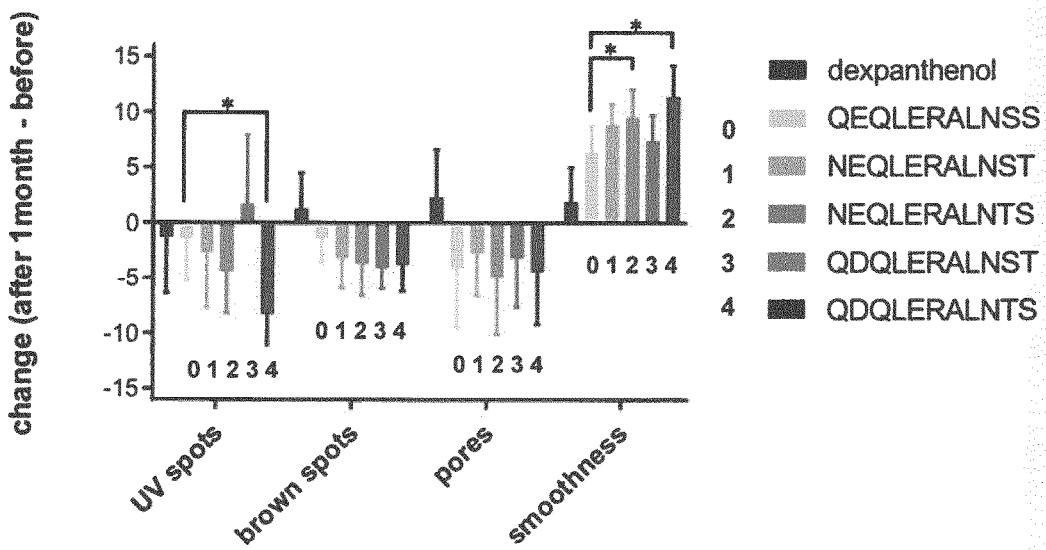
FIG. 2 shows the efficacy of the tested polypeptides (Peptides 0, 1, 2, 3 and 4) and UV spots, brown spots, pores and smoothness parameter changes after 1 month of formulation application.

FIG. 2: shows the efficacy of the tested polypeptides (Peptides 0, 1, 2, 3 and 4).

UV spots, brown spots, pores and smoothness parameter changes after 1 month of formulation application.

Reduction of UV spots, brown spots or pores and increase of smoothness is a cosmetic benefit. Bars represent mean change and standard deviation of the mean change. Statistical analysis was performed in GraphPad Prism 7 using a one-way ANOVA Significance levels are 0.05 (*) and 0.01 (**). Dexpanthenol (final 5% mass/mass) and the peptides were delivered by a cream.

Erythema Studies:

Another means of measuring the efficacy of tissue-protection exerted by any formulation is the speed of skin recovery from a UVB light-induced erythema such as common sunburns. Erythema are skin irritations with enhanced redness of the skin due to local hyperaemia (enhanced blood flow in superficial capillaries) that is associated with repair processes in the skin. The quicker the repair process is, the quicker the hyperaemia gets shut down and thus the quicker the skin redness gets reduced to normal levels. Accordingly, the redness can be measured as a proxy for the damage status of the skin.

In this assay, healthy subjects received the doubled minimal erythema dose (MED) on skin areas of about 1×1 cm$^2$ on the left arm. Beforehand, the MED was determined individually for each subject by exposing other skin areas to increasing intensities of UV light emitted by the UV6 lamp (280-360 nm) of the Waldmann UV 802 L device.

Immediately after exposure to the doubled MED the each 1×1 cm$^2$ area was treated with 20 µl of formulation or left untreated. The formulations used in these assay were dexpanthenol (5% mass/mass) or the tissue-protective peptides (QEQLERALNSS, NEQLERALNST, NEQLERALNTS, QDQLERALNST, or QDQLERALNTS) delivered by a lotion. Dexpanthenol, a provitamin of vitamin B$_5$, is commonly used in both cosmetic skin care creams and medical skin treatments and also exerts a tissue-protective effect in skin. Thus it was chosen as a control reference treatment.

Before light double MED exposure and after 6 hours, skin redness in the exposed area was spectroscopically measured using the 'chroma meter CR-400' manufactured by Konica Minolta. Redness of every area in every subject 6 hours after the exposure was normalized to the redness of the same area before the exposure by division of measured redness values.

All tested creams limited double MED-induced skin redness (erythema) in comparison to untreated skin. The peptide-delivery formulation of this invention in combination with the tissue-protective peptide QEQLERALNSS limited the erythema more efficiently than dexpanthenol. Moreover, the formulations with the tissue-protecive peptides of this invention (NEQLERALNST, NEQLERALNTS, QDQLERALNST or QDQLERALNTS) performed even better than the formulations with the previously described QEQLERALNSS peptide (see figure). Accordingly, skin areas treated with these formulations with novel peptides exhibited lower normalized skin redness values after.

Figure 3:
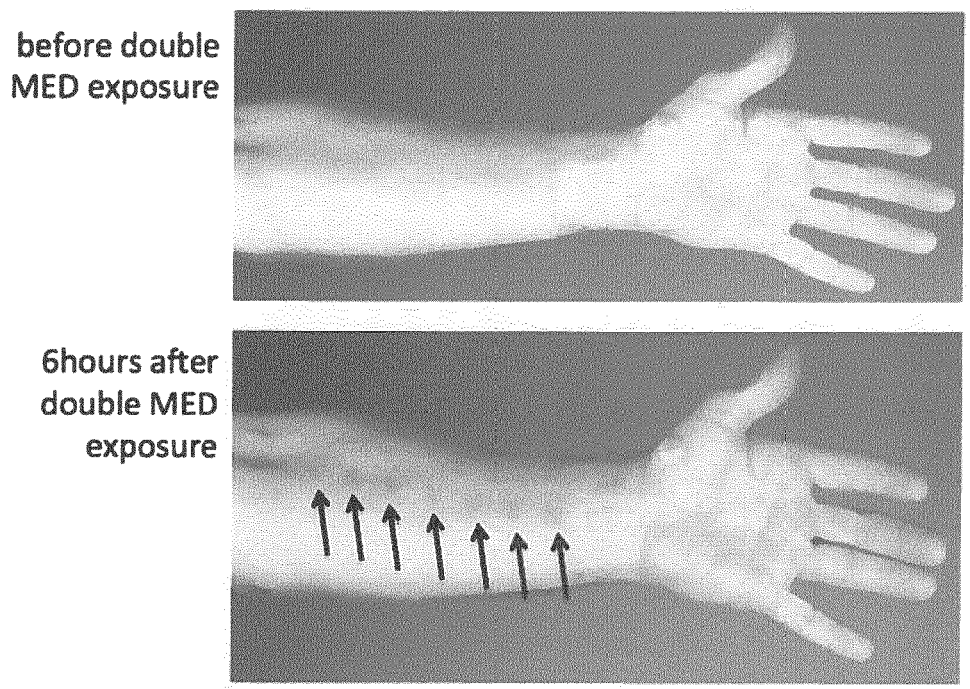
FIG. 3 shows images of skin recovery from UV light-induced erythema before and after exposure within 6 hours.
Figure 4:
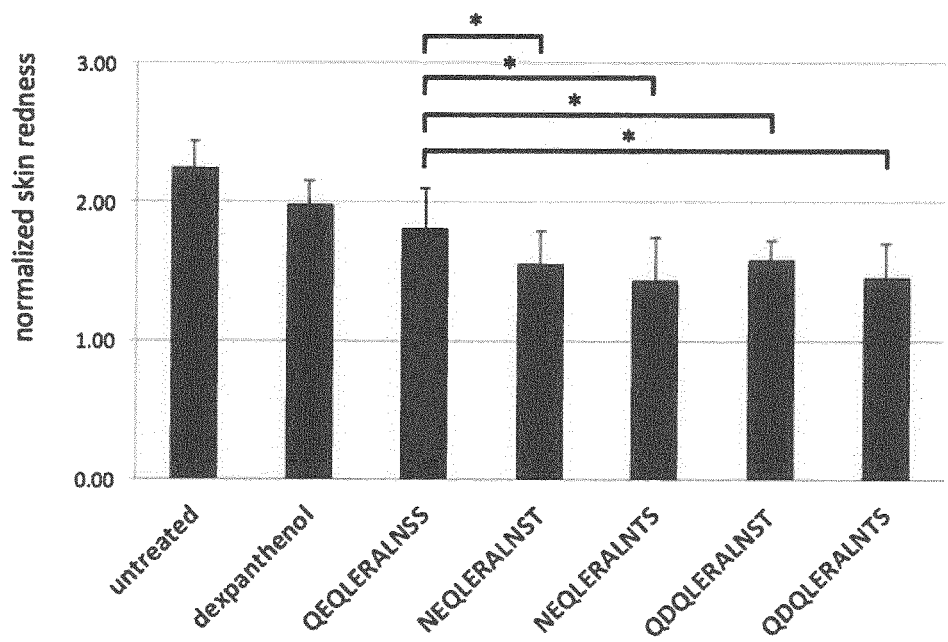
FIG. 4 shows the recovery from UV light-induced erythema within 6 hours in terms of inflammation measured as red light absorption.

FIG. 3: shows images of skin recovery from UV light-induced erythema before and after exposure within 6 hours FIG. 4: shows the recovery from UV light-induced erythema within 6 hours in terms of inflammation measured as red light absorption.

Red light absorption values were normalized to the value of the same skin area before UV light exposure by division. A normalized red light absorption value of 1 represents the skin state before UV light exposure. Reduction of the normalized red light absorption values towards 1 represents enhanced skin protection and recovery. Bars represent mean change and standard deviation of the mean change. Statistical analysis was performed in GraphPad Prism 7 using a one-way ANOVA. Significance levels are 0.05 (*) and 0.01 (**).

Dexpanthenol (final 5% mass/mass) and the peptides were delivered by the iARP lotion.

Acne Trial 1

The test person was a 25 year old lady with severe acne on the face and neck. She was treated for one week with a standard cosmetic formulation based on a control lipid (dexpanthenol/panthenol), but without a polypeptide according to the invention.

After one week the acne was slightly reduced.

Figure 5:
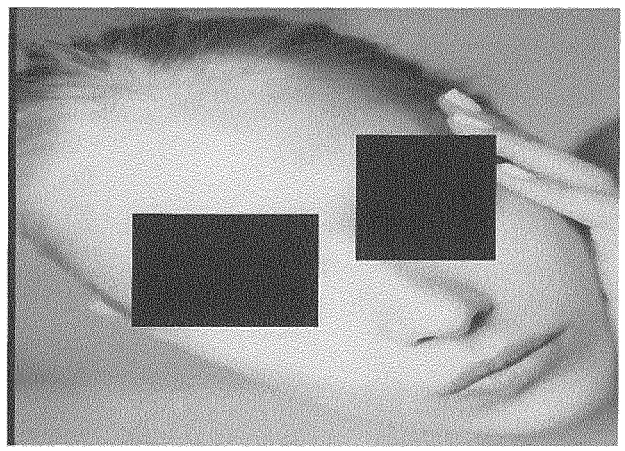
FIG. 5, lower image, shows that a test person, treated with the formulation of the invention, had visible improvement after one week a versus the panthenol formulation; the central image shows that a visible reduction of acne in the test person could be observed at week 3; and the upper image shows that the acne of the test person, after 8 weeks of treatment, has been completely reversed and the skin has become immaculate.
Figure 5:
Figure 5:
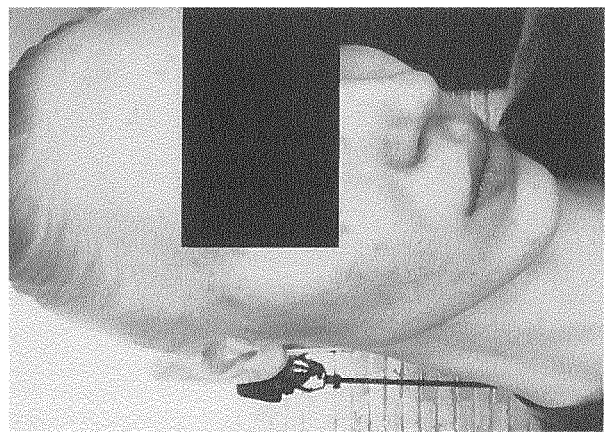

Then a cosmetic formulation according to the invention was applied, but again without a polypeptide according to the invention. The formulation contained ceramides and lecithin instead of dexpanthanol, and amino acids such as L-arginine. After one week a visible improvement versus the panthenol formulation of the art could be observed (FIG. 5, lower image).

The test person then was treated with a formulation of the invention now comprising "Peptide 0". At week 3 a slight but visible reduction of acne could be observed (FIG. 5, central image) Thereafter no further improvement was detectable during further treatment.

After 3 weeks the test person was treated with the same formulation but which now comprised "Peptide 4" instead of the reference polypeptide ("Peptide 0"). After one week a significant improvement could be observed. After 8 weeks treatment acne has been completely reversed and the skin has become immaculate (FIG. 5, upper image).

Relative Cosmetic Relevance in Over-all Skin-Protective Activity standard cosmetic lipid composition<lipid/amino acid composition of the invention without arginine<lipid/amino acid composition of the invention with arginine;

EPO<EPO fragments 1-3<Peptide 0, 1<Peptide 3<Peptide 2<Peptide 4

Acne Trial 2

Four test groups (corresponding to the "peptides, 0, 2, 3 and 4") with each five persons (in total, 20 subjects) suffering from acne, were treated twice daily with a formulation of the invention ("iARP-lotion" with trigger factor complex) for one week. No undesirable or even pathological lesions in the relevant skin area of the test persons were observed. So, it can be concluded that the practical application of all lotion sample products (containing peptide 0, 2, 3 or 4) did not trigger any unwanted skin reactions caused by skin-irritating or sensitizing effects.

The various peptides however lead to various effects using identical formulations (Table 3 and 4). They have both a physicochemical impact (peptide 4 stabilizes the formulation and consistency), or improved antihistaminic properties of peptide 3 compared to Peptide 0 (without any effect shown).

Peptides 2, 3 and 4 were superior compared to Peptide 0 in overall product evaluation.

Peptides 2 and 3 showed improved overall skin tolerance compatibility as excellent.

Peptide 4 was still rated good, but in the combination with product consistency it scored 200 versus 120-140 of Peptide 0 (sum of both scores).

Peptide 2 with the formulation according to the invention achieved the highest product overall score.

All formulations were 20% superior over Peptide 0 based formulations applied for acne.

TABLE 3

| Values for following parameters among 5 subjects tested | Peptide 0 | Peptide1 | Peptide 2 | Peptide 3 | Peptide 4 |
|---|---|---|---|---|---|
| Visable improvement of wrinkles | 1x | NT | — | — | — |
| Visable improvement of dryness | 4x | NT | 3x | 2x | 1x |
| Visable improvement of redness | 1x | NT | 1x | 1x | 1x |
| Visable improvement of itching | — | NT | — | 2x | — |
| Product evaluated overall as very good | 1x | NT | 1x | 1x | 0x |
| Product evaluated overall as good | 2x | NT | 3x | 3x | 3x |
| Product evaluated neither good or bad | 2x | NT | 1x | 1x | 2x |
| Product consistency exactly right | 4x | NT | 4x | 4x | 5x |
| Fresh and younger appearance clearly claimed after use | 2x | NT | 1x | 2x | 0x |
| Skin quality claimed to be clearly improved after use | 3x | NT | 2x | 1x | 1x |
| Less pick spots/lesions/pimple clearly claimed after use | 2x | NT | 1x | 1x | 0x |
| Less spots/lesions/blackhead clearly claimed after use | 2x | NT | 1x | 1x | 0x |
| Product use clearly refined skin texture | 2x | NT | 2x | 1x | 0x |
| Product use obviously refined pores | 2x | NT | 2x | 1x | 0x |
| Product use clearly improved skin structure | 2x | NT | 2x | 1x | 0x |
| Skin tolerance compatibility evaluated as excellent | 2x | NT | 4x | 3x | 0x |
| Skin tolerance compatibility evaluated as good | 1x | NT | 1x | 2x | 5x |
| Tested product will further recommend | 4x | NT | 5x | 4x | 3x |

NT: not tested

TABLE 4

| Values for followung parameters among 5 subjects tested | Peptide 0 | Peptide1 | Peptide 2 | Peptide 3 | Peptide 4 |
|---|---|---|---|---|---|
| Visable improvement of itching | 0% | NT | 0% | 40% | 0% |
| Product evaluated overall as good | 40% | NT | 60% | 60% | 60% |
| Product evaluated neither good or bad | 40% | NT | 20% | 20% | 40% |
| Product consistency exactly right | 80% | NT | 80% | 80% | 100% |
| Skin tolerance compatibility evaluated as excellent | 40% | NT | 80% | 60% | 0% |
| Skin tolerance compatibility evaluated as good | 20% | NT | 20% | 20% | 100% |
| Tested product will further recommend | 80% | NT | 100% | 80% | 60% |
| TOTAL | 300% | NT | 360% | 360% | 360% |

NT: not tested

General Observations:

The formulations of the invention are synergistic compositions which transport key ingredients to the skin leading to improved functional results over a control lipid (dexpanthenol). A major jump in safety is achieved if the known EPO mimetic peptides are changed in their structure to reduce their receptor binding activity known from the previous peptides. This is explained by still using them as transporter molecules which target the CD 90 cell microenvironment packed with key nutrients and vasodilating compounds (e.g arginine and others according to the invention). To bring the key nutrients and nourishing factors in the area (microenvironment) around the skin endogenous stem cells. This makes sure those skin cells can follow their physiologic role in skin repair and skin health. The formulations developed including especially lipid structures such as ceramides bind the molecule to the skin and prevent availability outside the skin.

In general, also the known EPO fragments (1-3, see above) and full length human EPO as active components in the cosmetic formulations and compositions according to the invention, above all in formulations comprising amino acids such as arginine and based on ceramide/phosphatidyl derived lipids show positive effects in erythema and acne studies.

The invention claimed is:

1. A cosmetic formulation or composition for topical administration of the skin, for skin repair, rejuvenation of skin, natural skin glow, reduction of wrinkles, anti-aging of skin, and avoidance and improvement of dry and ruptured skin, the formulation or composition comprising:

(i) at least one isolated tissue-protective polypeptide (tpP) consisting of 11 to 40 amino acids, wherein the tissue-protective polypeptide is an agonist of the EPO receptor (EpoR) and/or the common receptor (ßcR), targets CD90 expressing skin cells, and does not or not essentially elicit hematopoietic/erythropoietic activity, and is an EPO peptide variant, wherein the EPO variant comprises or is one of the amino acid sequences selected from the group consisting of:
NEQLERALNTS (SEQ ID NO: 12);
NEQLERALNST (SEQ ID NO: 13);
QDQLERALNTS (SEQ ID NO: 14);
QDQLERALNST (SEQ ID NO: 15), and (ii) a lipid compound, a composition of lipid compounds, or a lipid structure, wherein the tissue-protective polypeptide (tpP) is linked or associated to the lipid compound or lipid structure by ionic interaction or by covalent bonding, or is admixed therewith or embedded or encapsulated therein by forming a micelle or liposomal structure, and (iii) at least one triggering agent that stimulates vasculature relaxation and/or supports transport of the tissue-protective polypeptide (tpP) to the CD90 expressing skin cells, wherein the triggering agent stimulates nitric oxide (NO) and/or acetylcholine formation in the CD90 expressing skin cells.

2. The cosmetic formulation or composition according to claim 1, wherein the lipid compound or lipid structure is based on a sphingolipid, such as a ceramide, or phospholipid such as a phosphatidylcholine.

3. The cosmetic formulation or composition according to claim 1, wherein the triggering agent comprises one or more amino acids or amino acid derivatives, selected from the group consisting of arginine, phenylalanine, lysine, glutamine, tyrosine, tryptophan, valine, proline, citrulline, creatine, taurine, and a polypeptide comprising or consisting of two or more identical or different amino acids as specified.

4. The cosmetic formulation or composition according to claim 1, further comprising vitamin B5, and/or vitamin E, and/or choline.

5. The cosmetic formulation or composition according to claim 1, wherein the triggering agent is N-terminally and/or C-terminally linked to the tissue-protective polypeptide (tpP) by covalent bonding.

6. The cosmetic formulation according to claim 1, composed of:

(i) a cream or lotion base composition; and (ii) a composition comprising said tissue-protective polypeptide, a sphingolipid and/or a phospholipid, and one or more molecules, selected from the group consisting of arginine, phenylalanine, lysine, glutamine, tyrosine, tryptophan, valine, proline, citrulline, creatine, taurine, a polypeptide comprising or consisting of two or more identical or different such amino acids, vitamin B5, vitamin E, choline.

7. A conjugate molecule comprising of at least:

(a) a skin tissue-protective polypeptide (tpP) consisting of 11 to 40 amino acids, wherein the tissue-protective polypeptide (tpP) is an EPO peptide variant and does not or not essentially elicit hematopoietic/erythropoietic efficacy, wherein the EPO variant comprises or is one of the amino acid sequences selected from the group consisting of:

NEQLERALNTS (SEQ ID NO: 12);

NEQLERALNST (SEQ ID NO: 13);

QDOLERALNTS (SEQ ID NO: 14);

QDQLERALNST (SEQ ID NO: 15), and (b) a triggering agent that stimulates vasculature relaxation and/or supports transport of the tissue-protective polypeptide (tpP) to the CD90 expressing skin cells, wherein the triggering agent is selected from the group consisting of one or more molecules, selected from the group consisting of arginine, phenylalanine, lysine, glutamine, tyrosine, tryptophan, valine, proline, creatine, taurine, a polypeptide comprising or consisting of two or more identical or different such amino acids, vitamin B5, vitamin E, choline;

said skin tissue-protective polypeptide (tpP) being linked to said triggering agent by covalent bonding.

8. The conjugate molecule according to claim 7, further comprising a lipid compound, a composition of lipid compounds, or a lipid structure, wherein the conjugate molecule is linked or associated to the lipid compound or lipid structure by ionic interaction or by covalent bonding, or is admixed therewith or embedded or encapsulated therein by forming a micelle or liposomal structure.

9. The conjugate molecule according to claim 7 wherein the conjugate molecule is effective in the cosmetic treatment of skin, including skin repair, rejuvenation of skin, natural skin glow, reduction of wrinkles, anti-aging of skin, and avoidance and improvement of dry and ruptured skin.

10. An isolated polypeptide capable to bind to the erythropoietin receptor (EpoR) and/or the common a receptor (ßcR) consisting of one of the 11-mer amino acid sequences selected from the group consisting of:

NEQLERALNTS (SEQ 1 D NO: 12);

NEQLERALNST (SEQ ID NO: 13);

QDQLERALNTS (SEQ ID NO: 14); and

QDQLERALNST (SEQ ID NO: 15).

11. The isolated polypeptide according to claim 10, wherein the peptide is effective in the cosmetic treatment of skin, including skin repair, rejuvenation of skin, natural skin glow, reduction of wrinkles, anti-aging of skin, and avoidance and improvement of dry and ruptured skin.

12. The method for the cosmetic treatment of skin, including skin repair, rejuvenation of skin, natural skin glow, reduction of wrinkles, anti-aging of skin, and avoidance and improvement of dry and ruptured skin, the method comprising: administering topically the cosmetic formulation according to claim 1.

13. The method for the cosmetic treatment of skin, including skin repair, rejuvenation of skin, natural skin glow, reduction of wrinkles, anti-aging of skin, and avoidance and improvement of dry and ruptured skin, the method comprising: administering topically the conjugate molecule according to claim 7.

14. The method for the cosmetic treatment of skin, including skin repair, rejuvenation of skin, natural skin glow, reduction of wrinkles, anti-aging of skin, and avoidance and improvement of dry and ruptured skin, the method comprising: administering topically the isolated polypeptide according to claim 10.

* * * * *